US009421116B2

(12) United States Patent
Aramaki et al.

(10) Patent No.: US 9,421,116 B2
(45) Date of Patent: Aug. 23, 2016

(54) DIGESTIVE TRACT DEVICE

(71) Applicant: TERUMO KABUSHIKI KAISHA, Shibuya-ku (JP)

(72) Inventors: Naoki Aramaki, Atsugi (JP); Ryou Nakamoto, Hiratsuka (JP)

(73) Assignee: TERUMO KABUSHIKI KAISHA, Shibuya-Ku, Tokyo (JP)

( * ) Notice: Subject to any disclaimer, the term of this patent is extended or adjusted under 35 U.S.C. 154(b) by 134 days.

(21) Appl. No.: 14/472,546

(22) Filed: Aug. 29, 2014

(65) Prior Publication Data

US 2014/0371652 A1   Dec. 18, 2014

Related U.S. Application Data

(63) Continuation of application No. PCT/JP2013/053151, filed on Feb. 8, 2013.

(30) Foreign Application Priority Data

Mar. 1, 2012 (JP) ................................. 2012-045533
Mar. 1, 2012 (JP) ................................. 2012-045538
Mar. 1, 2012 (JP) ................................. 2012-045552

(51) Int. Cl.
*A61M 5/00* (2006.01)
*A61F 5/00* (2006.01)
*A61B 17/00* (2006.01)

(52) U.S. Cl.
CPC ..... *A61F 5/0076* (2013.01); *A61B 2017/00818* (2013.01)

(58) Field of Classification Search
CPC ................. A61F 5/0076; A61F 2017/00818; A61F 5/0069; A61F 5/0013; A61F 5/0026; A61F 5/0036; A61F 5/004; A61F 5/0079; A61F 2/04; A61F 2/24; A61F 2/07; A61F 2002/044; A61F 2002/045; A61F 2002/8483; A61F 2250/0039; A61F 2250/0067
USPC ............................................................ 604/8
See application file for complete search history.

(56) References Cited

U.S. PATENT DOCUMENTS 5,820,584 A     10/1998  Crabb
2008/0195226 A1*  8/2008  Williams ............... A61F 2/04
                                              623/23.67

FOREIGN PATENT DOCUMENTS

JP    2010-502289 A    1/2010
WO   WO 2010/074712 A2   7/2010

OTHER PUBLICATIONS

International Search Report (PCT/ISA/210) mailed on Mar. 12, 2013, by the Japanese Patent Office as the International Searching Authority for International Application No. PCT/JP2013/053151.

*Primary Examiner* — Philip R Wiest

(74) *Attorney, Agent, or Firm* — Buchanan Ingersoll & Rooney PC

(57) ABSTRACT

A digestive tract device is configured to reduce the burden on a living body associated with the adjustment of the length of a tubular portion retained inside the living body and simplify a retention operation after introducing the digestive tract device into the living body. The digestive tract device includes a tubular portion provided with a main body having a through hole extending in the longitudinal direction and a tip opening continuous with the through hole and a folded-back portion formed by folding back the main body in the longitudinal direction, a holding unit which holds the folded-back portion in a folded-back state with the tip opening open, and a retention unit which is provided on the base end side of the tubular portion and retains the tubular portion inside a living body.

19 Claims, 30 Drawing Sheets

DIGESTIVE TRACT DEVICE

CROSS-REFERENCES TO RELATED APPLICATIONS

This application is a continuation of International Application No. PCT/JP2013/053151 filed on Feb. 8, 2013, and claims priority to Japanese Application No. 2012-045533 filed on Mar. 1, 2012, Japanese Application No. 2012-045538 filed on Mar. 1, 2012 and Japanese Application No. 2012-045552 filed on Mar. 1, 2012, the entire content of all four of which is incorporated herein by reference.

TECHNICAL FIELD

The present invention generally relates to a digestive tract device configured to be placed inside the digestive tract.

BACKGROUND DISCUSSION

In recent years, it has been known that a bypass surgery in which the upper part of the stomach and the lower part of the small intestine are surgically directly connected to each other is effective as a method for treating diabetes (especially type 2 diabetes) and obesity. When such a bypass surgery is performed, the nutrients directly flow into the lower part of the intestine from the upper part of the stomach, and the nutrients therefore do not flow to the duodenum and the upper part of the jejunum both located on the upper part of the small intestine. As a result, it is possible to reduce the absorption of nutrients. Further, when the nutrients do not flow to the upper part of the small intestine, glucose-dependent insulinotropic polypeptide (GIP), glucagon and the like which are gastrointestinal hormones secreted in response to the stimulus of nutrients are not likely to be secreted. In addition, when the undigested nutrients pass through the lower part of the jejunum and the ileum both located on the lower part of the small intestine, the secretion of glucagon-like peptide-1 (GLP-1) which is a gastrointestinal hormone increases in response to the stimulus of the nutrients. GIP and glucagon are considered as factors which reduce the secretion of insulin. Therefore, when GIP and glucagon are not secreted, it becomes difficult to inhibit the secretion of insulin. Further, GLP-1 is considered a factor which accelerates the secretion of insulin. As described above, a bypass surgery is considered to exhibit an effect on the treatment of diabetes and obesity not only by restricting the absorption of nutrients, but also by accelerating the secretion of insulin by the action of the gastrointestinal hormone.

However, a bypass surgery is highly invasive. Therefore, in recent years, a low-invasive method in which a sleeve through which nutrients flow is placed on the upper part of the small intestine has been attracting attention. For example, a device provided with a tubular sleeve which can be placed inside the small intestine is described in Japanese Application Publication No. 2010-502289. The device can be orally placed and therefore has low invasiveness. Nutrients which have reached the pyloric ring are allowed to pass through the inside of the sleeve, so that the nutrients can reach the lower part of the small intestine without making contact with the upper part of the small intestine.

In such a device, an increase and decrease of nutrients absorbed by the small intestine depend on the length of the sleeve. Therefore, when reducing the efficiency of digestion and abruption of nutrients by the device after the sleeve is placed inside the small intestine, that is, when increasing the effect obtained by the device, the length of the sleeve may be adjusted to be longer.

SUMMARY

When placing the device described in Japanese Application Publication No. 2010-502289, the sleeve is introduced into the small intestine with its distal end part closed. Then, when the sleeve is introduced into the small intestine, the distal end part thereof is opened and expanded in the longitudinal direction. Although it is possible to extend a part of the sleeve while opening and expanding the distal end part of the sleeve during the placement, it is not possible to adjust the length of the sleeve after the sleeve is placed inside the small intestine. Therefore, when reducing the absorption of nutrients in the small intestine after the placement, it is necessary to perform an operation of temporarily taking out the device from the small intestine, and introducing another device that is provided with a sleeve having a different length into the small intestine. Performing such a replacement operation imposes a heavy burden on a living body. Further, when using the sleeve, it is necessary to open the distal end of the sleeve inside a living body. Therefore, a complicated operation is forced from when the sleeve is introduced into the living body until when the device is brought to a usable state.

The digestive tract device disclosed here is configured to reduce the burden on a living body associated with the adjustment of the length of a tubular portion retained inside the living body and simplify a retention operation after introducing the digestive tract device into the living body.

The digestive tract device includes a tubular portion having a through hole, a retention unit that is provided in the tubular portion and holds the tubular portion inside a living body, a length adjustment unit that adjusts the length of the tubular portion and has a holding unit that holds at least a part of the tubular portion to adjust the length of the tubular portion.

The digestive tract device having the above configuration makes it possible to rather easily adjust the length of the tubular portion by releasing the holding of the tubular portion by the holding unit after introducing the digestive tract device into a living body or changing the position of the tubular portion held by the holding unit. Therefore, when increasing/reducing the digestion and absorption of nutrients in the stomach and the small intestine, it is not necessary to perform a complicated operation of replacing the tubular portion. As a result, it is possible to rather easily adjust the length of the tubular portion after the placement and reduce the burden on a living body associated with the length adjustment.

Further, when the holding unit holds the tubular portion in a folded-back state with a tip opening thereof open, it is possible to extend the tubular portion in the longitudinal direction by a relatively simple operation of pulling the folded-back portion after the placement or along with a decrease in the holding power with the lapse of time after the placement. Therefore, it is not necessary to perform a complicated operation of temporarily taking out the tubular portion from the small intestine and introducing another tubular portion having a different length into the small intestine when adjusting the length of the tubular portion to be longer after the placement. Thus, it is possible to reduce the burden on a living body associated with the adjustment of the length of the tubular portion retained inside the living body. Further, because the holding unit holds the folded-back portion in a folded state with the tip opening of the tubular portion open without blocking the tip opening, it is not necessary to perform an operation of opening the tip of the tubular portion inside a living body when using the digestive tract device. Therefore, a preparatory operation from when the digestive tract device is introduced into a living body until when the digestive tract device is made usable can be performed in a relatively simple manner.

Further, the holding unit includes at least a first holding region and a second holding region having different holding strengths for holding the folded-back portion in a folded-back state, and the first holding region is provided on the base end side with respect to the second holding region and the holding power of the first holding region is larger than the holding power of the second holding region. Therefore, when introducing and placing the digestive tract device inside a living body, it is possible to prevent the tubular portion from carelessly extending because of a decrease in the holding strength of the holding unit caused by contact with the living body.

The holding unit can include a thermally-fused portion to which the folded-back portion is bonded by thermal fusion, the holding unit can be formed on the tubular portion by a relatively simple method using thermal fusion. In addition, it is possible to relatively easily adjust the holding strength in the holding unit.

Further, the holding unit includes a biocompatible thread which sutures the folded-back portion, and so the tubular portion can be extended by a relatively simple operation of pulling the thread or with the lapse of time after the placement.

Further, the tip end of the main body continuous with the folded-back portion is located on the tip side of the tubular portion with respect to a tip-side folding back position of the folded-back portion when the holding unit holds the folded-back portion, and so it is possible to reduce the length of the tubular portion while maintaining the folded-back portion in a folded-back state by the holding unit by cutting a surplus portion located on the tip side of the main body. Accordingly, the digestive tract device is provided with a length adjustment mechanism for extending the length of the tubular portion which includes the folded-back portion and the holding unit and a length adjustment mechanism that makes it possible to reduce the length of the tubular portion by performing an operation such as cutting. Therefore, it is possible to adjust the length of the tubular portion to be longer or shorter within a predetermined range after introducing the tubular portion into a living body. Thus, it is possible to provide the digestive tract device capable of further improving the flexibility of procedures.

The length between the tip-side folding back position of the folded-back portion and the tip end of the main body is greater than the length between the tip-side folding back position of the folded-back portion and the retention unit, and so the length between the tip-side folding back position of the folded-back portion and the tip end of the main body is relatively long. Therefore, a relatively long length of the surplus portion which enables the length adjustment can be ensured. As a result, it is possible to provide the digestive tract device with better usability.

Further, the tip end of the main body continuous with the folded-back portion is located on the base end side of the tubular portion with respect to the tip-side folding back position of the folded-back portion when the holding unit holds the folded-back portion, and so a surplus portion which extends to the tip side from the tip opening when introducing the tubular portion into a living body is not formed on the tubular portion. Therefore, a decrease in the holding power of the holding unit caused by contact between the surplus portion and a living body is not caused when introducing the tubular portion into the living body. As a result, it is possible to effectively prevent careless extension of the tubular portion caused by a decrease in the holding power of the holding unit.

Further, the holding unit holds at least a part of the tubular portion in a lifted state toward the base end side, and so the length of the tubular portion can be returned to its original length by releasing the holding by the holding unit. Therefore, it is possible to reversibly adjust the length of the tubular portion after the digestive tract device is placed in a living body.

The holding unit includes a first locking piece attached to the tubular portion and a second locking piece that is attached to the tip side of the tubular portion with respect to the first locking piece and can be freely engaged with and disengaged from the first locking piece. It is possible to reduce the length of the tubular portion by a relatively simple operation of locking the first locking piece and the second locking piece to each other. Further, it is possible to return the length of the tubular portion to its original length by a relatively simple operation of releasing the locking between the first locking piece and the second locking piece.

Further, the second locking piece is freely deformable between a first shape that enables the second locking piece to move to the base end side of the tubular portion beyond the first locking piece and a second shape that enables at least a part of the second locking piece to be locked to the first locking piece on the base end side with respect to the first locking piece. It is thus possible to adjust the length of the tubular portion by a relatively simple operation of moving the second locking piece deformed in the second shape to a position on the base end side with respect to the first locking piece.

Also, the insertion holes through which an introduced object such as food can pass are formed on both the first locking piece and the second locking piece and the second locking piece is freely deformable to the second shape that enables the second locking piece to be inserted through the insertion hole of the first locking piece. It is thus possible to allow an introduced object such as food to smoothly flow down inside the tubular portion regardless of the placement of the first locking piece and the second locking piece.

Additionally, a plurality of first locking pieces are arranged in the longitudinal direction of the tubular portion so as to be separated from each other, and so the length of the tubular portion can be adjusted in a multistage manner. Therefore, it is possible to provide the digestive tract device with more improved usability.

The second locking piece includes an elastic member that is deformable between the first shape and the second shape, and so the second locking piece can be locked to the first locking piece by elastically deforming the second locking piece. Therefore, an operation required for the length adjustment can be more easily performed.

Further, the retention unit is provided on the base end side in a penetration direction of the tubular portion, such that the digestive tract device can be held to a living body in a region located on the upstream side of the flow of an introduced object such as food with respect to the duodenum. Therefore, it is possible to reliably prevent the occurrence of detachment even when retaining the digestive tract device for a long period of time.

Further, the retention unit is provided in a predetermined region between the base end and the tip of the tubular portion, and so it is possible to hold the digestive tract device in the pyloric ring and allows the base end side of the tubular portion to extend up to the cardia located on the upper part of the stomach. Therefore, it is possible to prevent food or the like from being introduced into the stomach.

According to another aspect, a digestive tract device positionable in a digestive track of a living body comprises: a tubular portion configured to be positioned in the digestive tract of the living body, with the tubular portion possessing a distal tip and a through hole opening at the distal tip of the tubular body; a retention unit positioned on a distal portion of the tubular portion, and a tubular body. The retention unit comprises one of: i) an outwardly expandable member that is outwardly expandable to an expanded state larger than a portion of the digestive tract when the distal portion of the tubular body is located in the digestive tract to hold the tubular body in the digestive tract; and ii) an expanded member larger than the portion of the digestive tract when the distal portion of the tubular body is located in the digestive tract to hold the tubular body in the digestive tract. The tubular body includes a folded portion at which the tubular body is folded in a folded condition of the tubular body, and the folded portion of the tubular body is held in the folded condition. The folded condition of the tubular body is releasable when the tubular body in the folded condition is positioned in the digestive tract to increase a length of the tubular body.

In accordance with another aspect, a method comprises: introducing a tip end portion of a tubular body into a digestive tract in a living body, with the tubular portion possessing a through hole and including a folded portion at which the tubular body is folded. The method also involves moving the tubular body with the folded portion in the digestive tract to a predetermined position in the digestive tract, and increasing the length of the tubular body located at the predetermined position in the digestive tract by unfolding the folded portion.

DETAILED DESCRIPTION

Hereinbelow, embodiments of the digestive tract device, representing examples of the digestive tract device disclosed here, will be described with reference to the drawings. For convenience of explanation and understanding, the dimensional ratio in each of the drawings may be exaggerated and may therefore differ from the actual ratio.

First Embodiment

Figure 1:
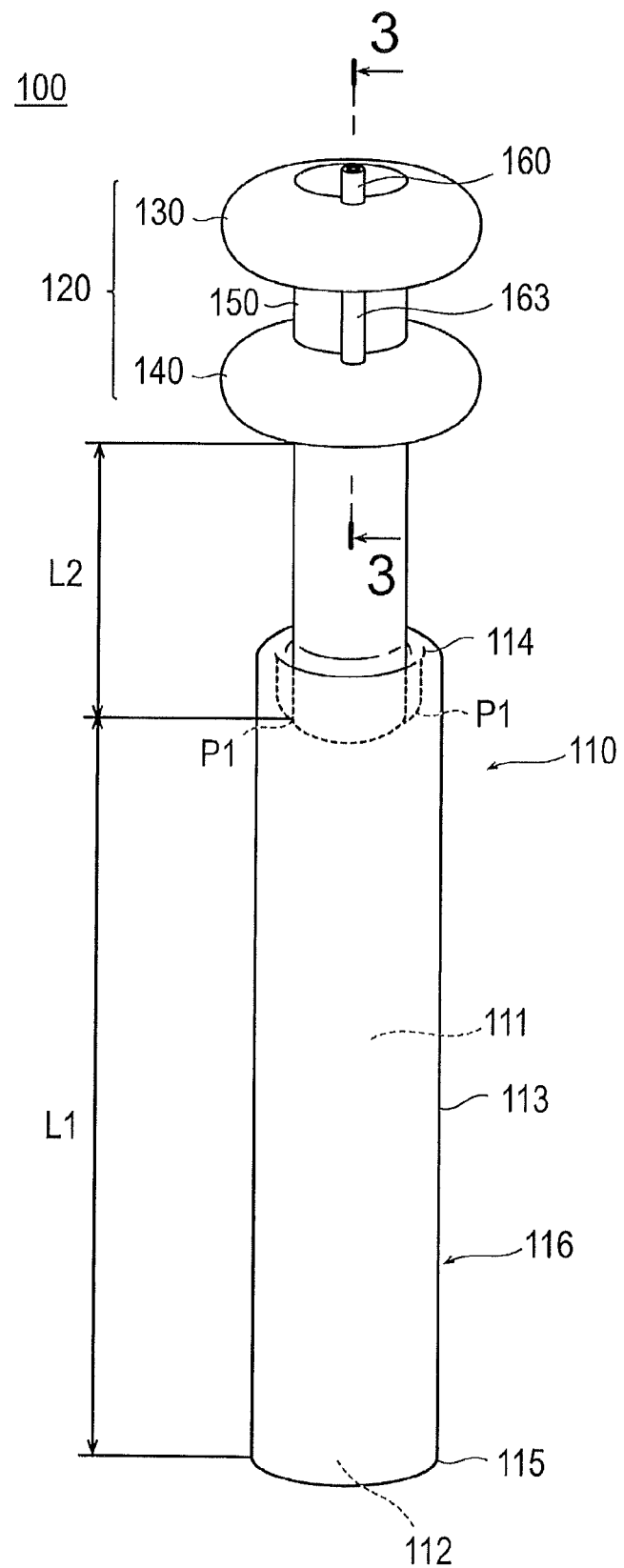
FIG. 1 is a perspective view of a digestive tract device according to a first embodiment representing one example of the digestive tract device disclosed here.
Figure 2:
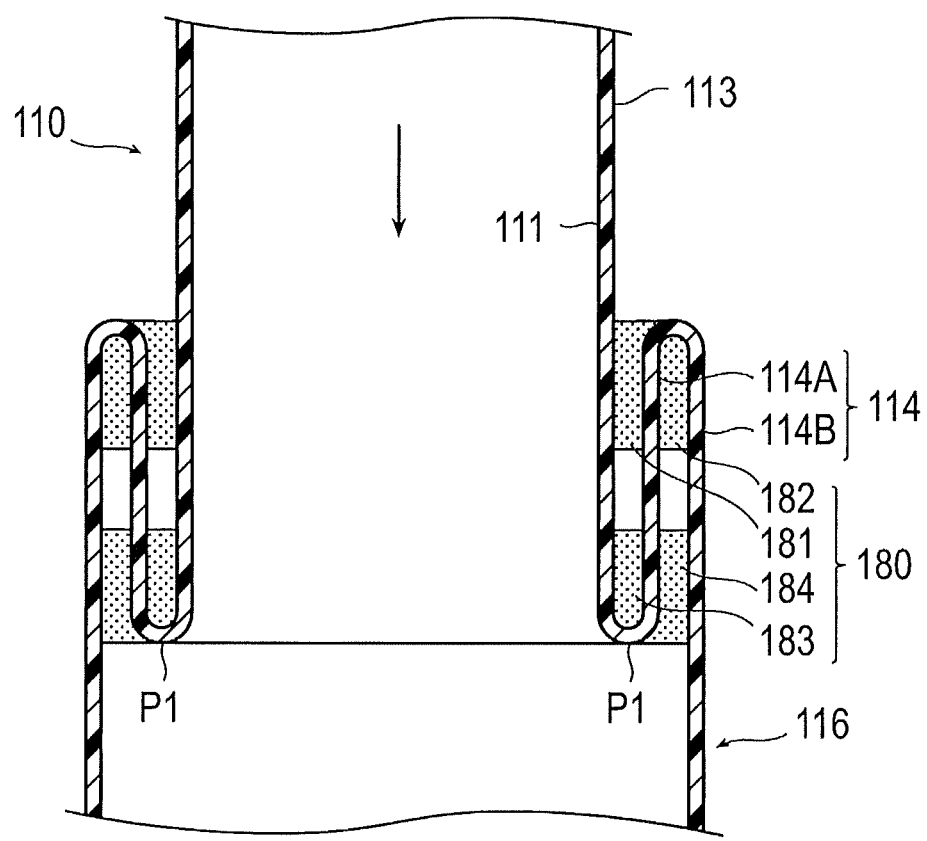
FIG. 2 is an enlarged cross-sectional view that illustrates a folded-back portion and the vicinity of the folded-back portion according to the first embodiment.
Figure 3:
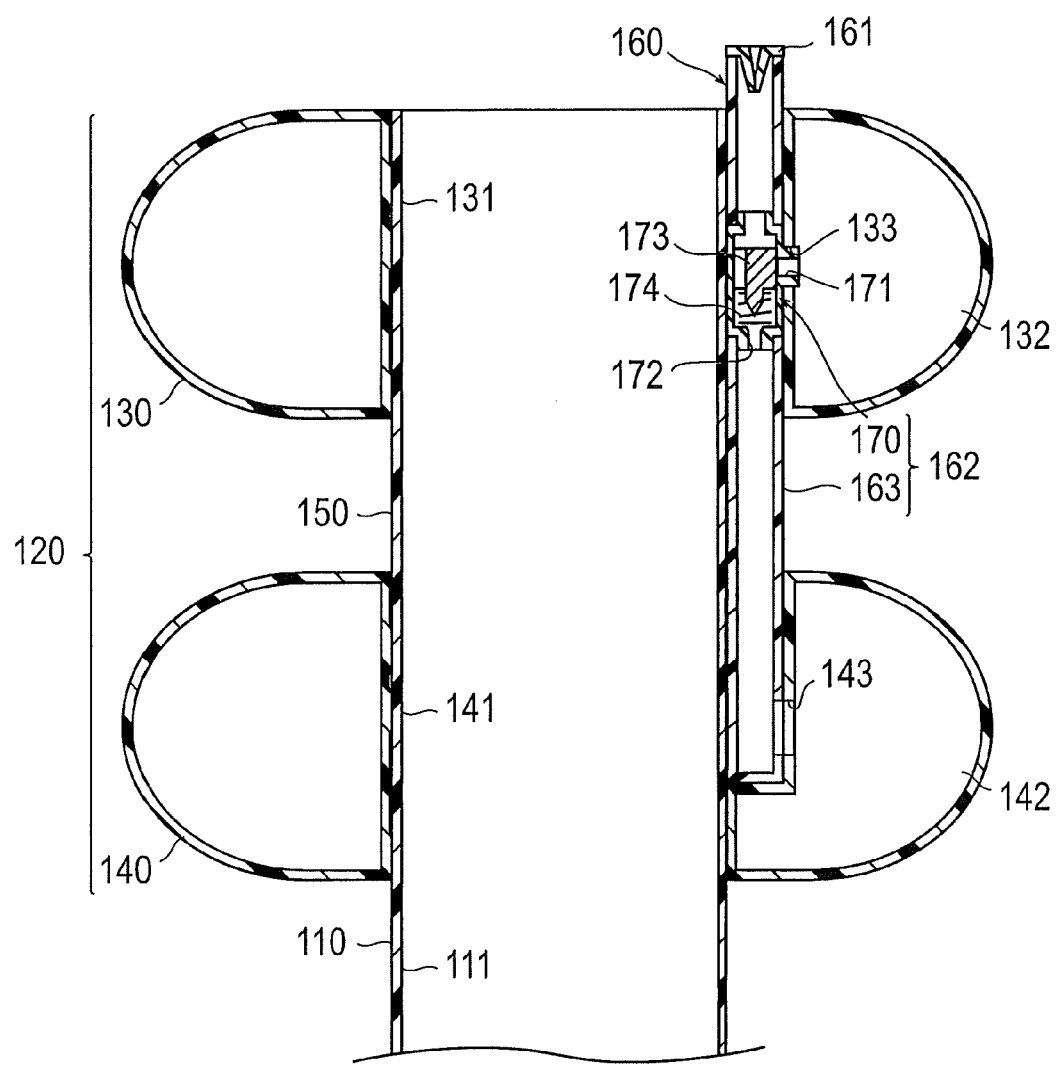
FIG. 3 is a cross-sectional view taken along the section line 3-3 of FIG. 1.

Referring to FIGS. 1-3, the digestive tract device 100 according to the present embodiment is orally or nasally inserted into the digestive tract and placed so as to cover a part of the digestive tract, and allows the ingested food to flow without making contact with the part of the digestive tract, the part being covered by the digestive tract device 100. As illustrated in FIGS. 1 and 2, the digestive tract device 100 includes a tubular portion 110 which has a main body 113 and a folded-back portion 114. The main body 113 has a through hole 111 extending in the longitudinal direction and a tip opening 112 continuous with, and in communication with, the through hole 111. The folded-back portion 114 is formed by folding back the main body 113 in the longitudinal direction.

The digestive tract device 100 further includes a holding unit 180 which holds the folded-back portion 114 in a folded-back state with the tip opening 112 open and a retention unit 120 which is provided on the base end side of the tubular portion 110 and retains the tubular portion 110 inside a living body. The holding unit 180 functions as a length adjustment unit which adjusts the entire length of the tubular portion 110 by holding a predetermined part of the tubular portion 110 or releasing the holding.

Hereinbelow, in the digestive tract device 100, a side at which the tubular portion 110 is provided is referred to as the tip side and a side at which the retention unit 120 is provided is referred to as the base end side. Further, inside the digestive tract, the anus side is referred to as the distal side and the mouth side is referred to as the proximal side.

As illustrated in FIG. 3, the retention unit 120 is provided with a first outwardly expandable unit 130 and a second outwardly expandable unit 140 which are arranged along a penetration direction (axial direction or longitudinal direction) of the tubular portion 110, a connection unit 150 which connects the first expandable unit 130 and the second expandable unit 140 to each other, and an inlet unit 160 which allows fluid to flow into the first expandable unit 130 and the second expandable unit 140. The fluid is, for example, a physiological saline solution. However, the fluid may also be another liquid, gas such as air, liquid or gas in which a solid is dispersed, and an aggregate of particles. Further, the fluid may be a mixture of liquid and gas so as to absorb a strong compression force from the digestive tract by the compressive gas while maintaining a relatively strong holding power by the non-compressive liquid.

The connection unit 150 is integrally formed with the tubular portion 110 into a tubular shape using the same material as the material of the tubular portion 110. The outer diameter of the connection unit 150 is equal to the outer diameter of the tubular portion 110 in the present embodiment. However, the outer diameter of the connection unit 150 may differ from the outer diameter of the tubular portion 110. The connection unit 150 may be formed of another material that differs from the material of the tubular portion 110. For example, the connection unit 150 may be integrally formed with the tubular portion 110 using the same material as the material of the first expandable unit 130 and the second expandable unit 140. Further, the connection unit 150 may have a shape other than a tubular shape. For example, the connection unit 150 may be provided only in a part of the tubular portion 110 in the circumferential direction, or may be provided so as to be divided into a plurality of pieces in the circumferential direction (a plurality of circumferential pieces).

The first expandable unit 130 is a ring-shaped balloon which is arranged on the base end side of the connection unit 150. A first hole 131 (an axially extending first hole) on the center of the ring communicates with the through hole 111 of the tubular portion 110. A first inlet space 132 is formed inside the first expandable unit 130, and fluid supplied from the outside can flow into the first inlet space 132 through a first inlet hole 133. The first hole 131 forms a space into which food flows and plays a role of guiding food to a second hole 141 (described below) of the second expandable unit 140 and the through hole 111 of the tubular portion 110.

The second expandable unit 140 is a ring-shaped balloon which is arranged on the tip side of the connection unit 150. The second hole 141 (an axially extending second hole) on the center of the ring communicates with the through hole 111 of the tubular portion 110. A second inlet space 142 is formed inside the second expandable unit 140, and fluid supplied from the outside can flow into the second inlet space 142 through a second inlet hole 143. The second hole 141 forms a space into which food flows from the first hole 131 of the first expandable unit 130 and plays a role of guiding food to the through hole 111 of the tubular portion 110.

The first expandable unit 130 and the second expandable unit 140 are each formed of an elastically deformable silicone resin. The first expandable unit 130 and the second expandable unit 140 may each be formed of, for example, another elastically deformable material such as natural rubber and a fluoro-silicone polymer. Further, a configuration in which a folded and contracted state is opened and expanded by allowing fluid to flow thereinto can also be employed. In this case, the first expandable unit 130 and the second expandable unit 140 may not be necessarily formed of an elastic material.

The first expandable unit 130 can be expanded preferably up to approximately 5 mm to 60 mm in its outer diameter. The length or axial extent of the first expandable unit 130 is preferably 30 mm to 50 mm. The second expandable unit 140 can be expanded preferably up to approximately 10 mm to 50 mm in its outer diameter. The length or axial extent of the second expandable unit 140 is preferably 30 mm to 50 mm. The distance between the first expandable unit 130 and the second expandable unit 140 is preferably 10 mm to 60 mm. However, the dimensions of the first expandable unit 130 and the second expandable unit 140 are not limited to these dimensions.

The inlet unit 160 is provided with a backflow prevention unit 161 which allows fluid from the outside to flow into the inlet unit 160 and prevents the backflow of the fluid temporality flowing into the inlet unit 160, and an adjustment unit 162 which adjusts the flow of fluid from the outside so as to expand the second expandable unit 140 prior to expanding the first expandable unit 130.

The backflow prevention unit 161 is a duck bill type check valve which allows fluid from the outside to flow into the inlet tube 160 and prevents the backflow of the fluid temporality flowing into the inlet tube 160. However, the structure of the backflow prevention unit 161 is not limited as long as it can prevent the backflow of fluid flowing from the outside.

The adjustment unit 162 is provided with a flow path tube 163 which extends from the base end side of the first expandable unit 130 up to the second expandable unit 140 and a flow path switching unit 170 which switches the flow path to the first expandable unit 130 and the second expandable unit 140.

The flow path tube 163 is a tubular body which is located near the holes of the first expandable unit 130 and the second expandable unit 140 (on the inner peripheral side) and guides fluid supplied from the outside to the first expandable unit 130 and the second expandable unit 140. The flow path tube 163 is formed of a silicone resin, a fluoro-silicone polymer, or the like. However, the material of the flow path tube 163 is not particularly limited.

The flow path switching unit 170 is arranged in the intermediate part of the flow path tube 163, and provided with a first flow path 171 which guides the fluid to the first inlet hole 133 of the first expandable unit 130, a second flow path 172 which guides the fluid to the second inlet hole 143 of the second expandable unit 140, a switching member 173 which moves in response to the pressure of fluid, and an elastic member 174 which biases the switching member 173.

The switching member 173 is biased at a position for blocking a flow path between the inlet unit 160 and the first flow path 171 and the second flow path 172 when the supply of the fluid is stopped, and biased by the elastic member 174 at a position for blocking the first flow path 171 and opening the second flow path 172 when the pressure of the fluid is low. When the pressure of the fluid increases, the switching member 173 is pushed by the fluid and moved to a position for blocking the second flow path 172 and opening the first flow path 171. In other words, the second expandable unit 140 is expanded when the pressure of the fluid is low, and the first expandable unit 130 is expanded when the pressure increases. Further, both the first flow path 171 and the second flow path 172 may also be opened by adjusting the pressure of the fluid. Further, when the supply of the fluid is stopped, the switching member 173 may also be biased to a position for blocking the first flow path 171, a position for blocking the second flow path 172, or a position for blocking a flow path between the first flow path 171 and the second flow path 172.

As illustrated in FIG. 2, the tubular portion 110 is formed in a hollow cylindrical shape having the through hole 111 which penetrates the tubular portion 110 in the longitudinal direction. The through hole 111 is substantially coaxial with the center axis of the retention unit 120 and extends in the axial direction.

The main body 113 includes the folded-back portion 114 which is formed by folding back a part of the main body 113 and an unfolded portion which substantially vertically extends to the tip side. The tip opening 112 of the main body 113 remains open both when the folded-back state of the folded-back portion 114 is maintained and when the folded-back state is released.

The folded-back portion 114 can be configured to have, for example, a folded-back portion 114A which is formed by folding back the main body 113 to the base end side and a folded-back portion 114B which is formed by folding back the main body 113 at the folded-back portion 114A toward the tip side. The folded-back portion 114 is preferably formed on the tip side of the tubular portion 110 as illustrated in FIG. 1 so that the extension of the tubular portion 110 can be rather easily realized or achieved when the folded-back state is released artificially or with the lapse of time. Further, the number of times of folding-back is not particularly limited as long as the main body 113 is folded back on itself at least once toward the base end side and once toward the tip side.

In the present embodiment, the holding unit 180 includes a thermally-fused portion which is formed by thermally fusing a part of the tubular portion 110. For example, the holding unit 180 can be formed to hold two places between the main body 130 and the folded-back portion 114A and between the folded-back portion 114A and the folded-back portion 114B.

As illustrated in FIGS. 1 and 2, when the holding unit 180 holds the folded-back portion 114, a tip end 115 of the main body 113 continuous with the folded-back portion 114 can be arranged on the tip side of the tubular portion 110 with respect to a tip-side folding back position P1 of the folded-back portion 114 (a tip-side holding back position of the folded-back portion 114A). A part of the main body 113, the part extending down to the tip side from the folding back position P1, constitutes a surplus portion 116 for adjusting the length of the tubular portion 110 to be shorter. When the surplus portion 116 is provided, it is possible to adjust the length of the main body 113 to be shorter by cutting the surplus portion 116 with a forceps with a blade or the like after inserting the tubular portion 110 into a living body. As illustrated in FIG. 1, the tubular portion 110 is folded back on itself so as to maintain the tip opening 112 in an open state. Therefore, the open state of the tip opening 112 is maintained before and after cutting the surplus portion 116. Thus, the length can be reduced by a relatively simple operation of merely cutting the surplus portion 116.

Further, for example, a length L1 between the folding back position P1 and the tip end 115 of the main body 113 can be made longer than a length L2 between the folding back position P1 and the retention unit 120. Such a configuration makes it possible to ensure a relatively long length of the surplus portion 116 which enables length adjustment. Therefore, it is possible to expand the range of the length adjustment for reducing the length and improve the flexibility of procedures using the digestive tract device 100.

The holding unit 180 can be formed to have different holding strengths in the longitudinal direction. In the illustrated form, the holding power or holding strength of first holding regions 181, 182 located on the base end side is larger than the holding power or holding strength of second holding regions 183, 184 located on the tip side. Therefore, the holding of the folded-back portion 114 by the holding unit 180 is first released in the first holding regions 181, 182, and thereafter released in the second holding regions 183, 184. For example, when the tubular portion 110 makes contact with the wall of the duodenum or the like when placing the digestive tract device 100, a folded-back state of the folded-back portion 114 may be disadvantageously released. When the holding power or holding strength of the first holding regions 181, 182 is relatively large as described above, the holding by the holding unit 180 is not so easily released. Therefore, it is possible to prevent the tubular portion 110 from being carelessly extended when introducing the tubular portion 110.

Although a method for allowing the holding regions to have different holding powers is not particularly limited, for example, it is possible to employ a method for varying the temperature, the pressure to be applied, the bonding time and the like in thermal fusion when forming the holding unit 180.

The thickness of the tubular portion 110 is preferably 0.002 mm to 0.02 mm. The outer diameter of the tubular portion 110 is preferably 10 mm to 60 mm. The length (axial length) in the penetration direction of the tubular portion 110 is preferably 600 mm to 1300 mm. However, the dimensions of the tubular portion 110 are not necessarily limited to these dimensions.

Although the tubular portion 110 is formed of polytetrafluoroethylene (PTFE) in the present embodiment, the material used to fabricate the tubular portion 110 is not limited to such material as long as the tubular portion 110 is formed to be flexible and deformable. For example, polyethylene, a silicone resin, polyurethane and the like may be used. The above-described dimensions of the tubular portion 110 can be appropriately changed depending on the material applied to the tubular portion 110.

Next, a method for placing the digestive tract device 100 according to the first embodiment inside the digestive tract will be described.

Figure 4:
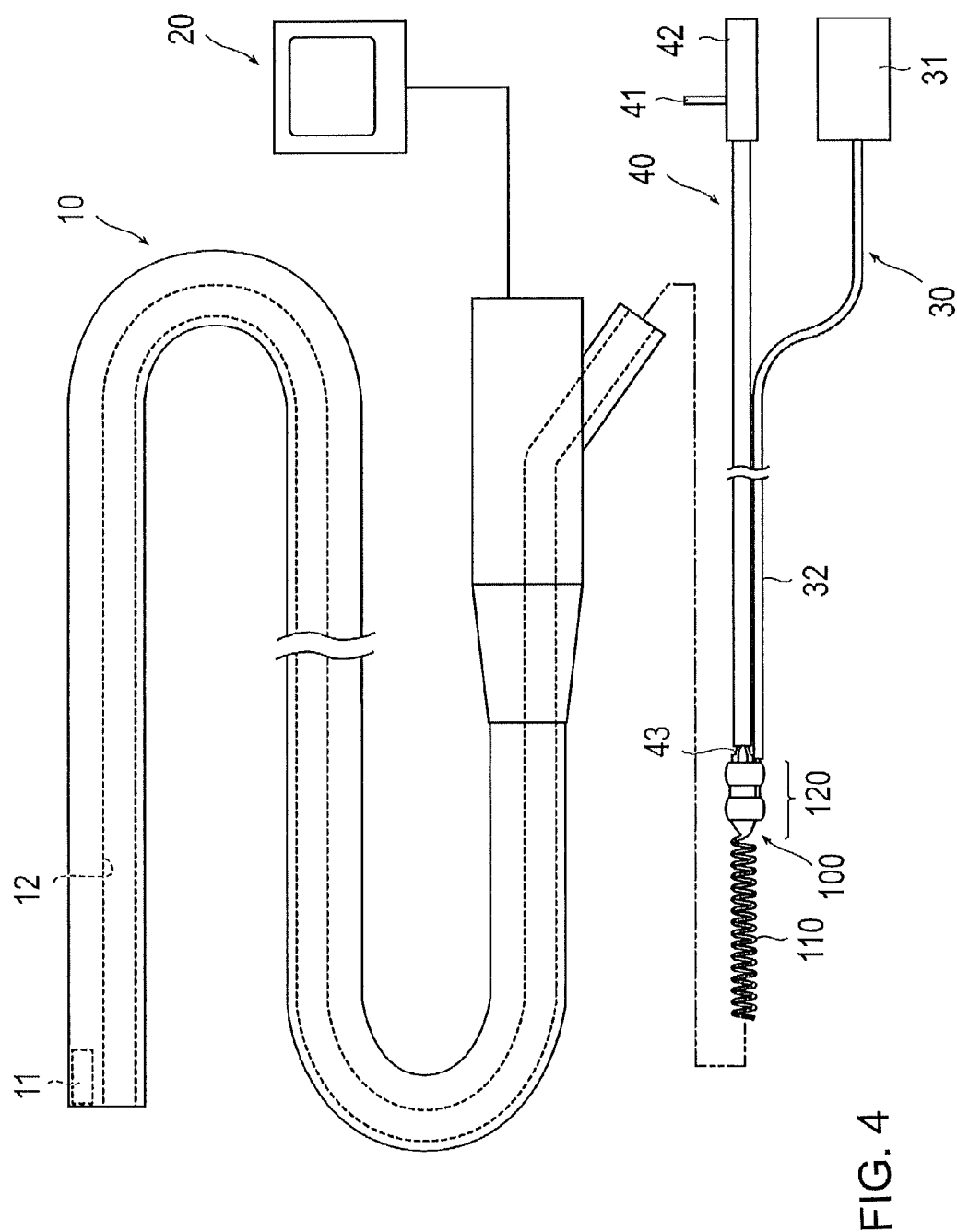
FIG. 4 is a schematic view of a digestive tract device placing system for placing the digestive tract device according to the first embodiment inside the digestive tract.
Figure 5:
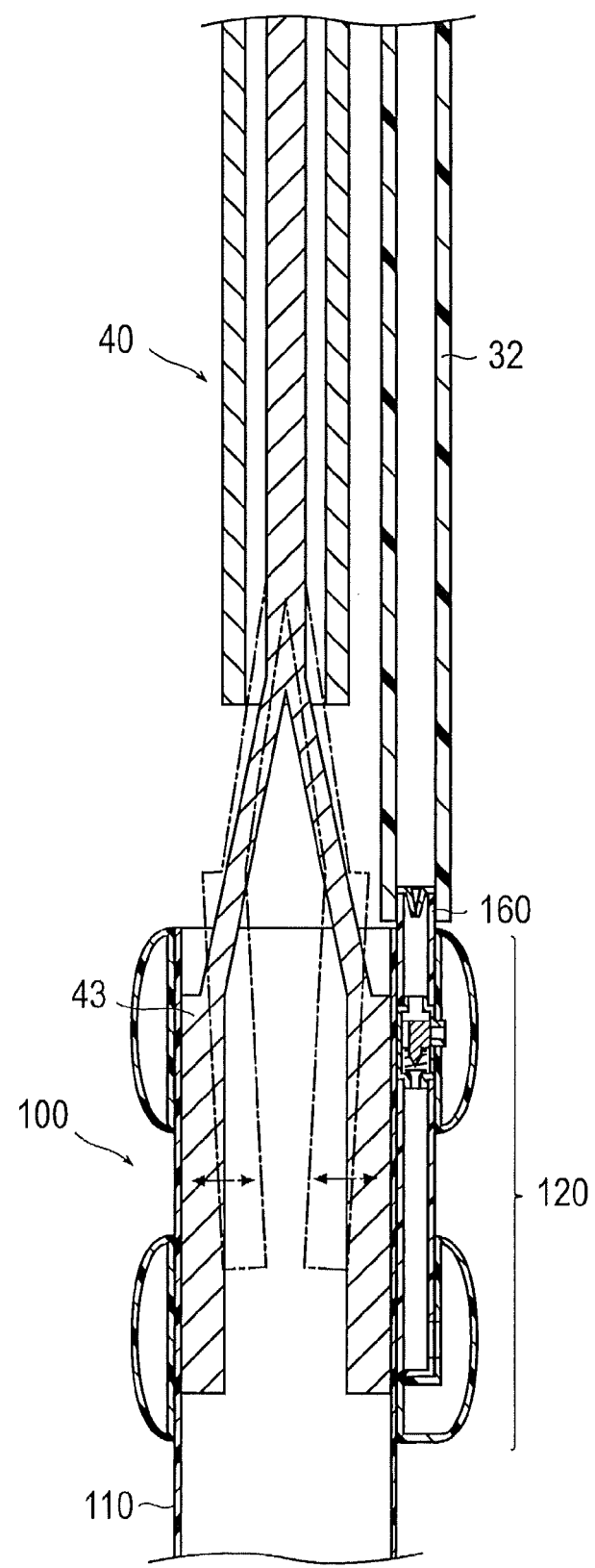
FIG. 5 is a cross-sectional view that illustrates a state in which a grasping member and a supply tube are connected to the digestive tract device according to the first embodiment.

When placing the digestive tract device 100 inside the digestive tract, an endoscope 10, a display device 20, a fluid supply device 30, and a grasping device 40 are used as illustrated in FIGS. 4 and 5. In other words, the digestive tract device 100, the endoscope 10, the display device 20, the fluid supply device 30, and the grasping device 40 together constitute the digestive tract device placing system for placing the digestive tract device inside the digestive tract.

The endoscope 10 is provided with an imaging element 11 which includes a CCD sensor or the like for performing imaging and a channel 12 which receives the digestive tract device 100 and for inserting the digestive tract device 100 into a living body. A general endoscope can be used as the endoscope 10. The configuration of the endoscope 10 is not particularly limited as long as it can perform imaging and the insertion of the digestive tract device 100.

The display device 20 is provided with a monitor which displays an image obtained by the endoscope 10.

The fluid supply device 30 is provided with a pressure device 31 which can supply a physiological saline solution as the fluid at any pressure and a supply tube 32 having one end which is connected to the pressure device 31 to allow the fluid to flow therethrough and the other end which can be liquid-tightly connected to the inlet unit 160 of the digestive tract device 100.

Figure 6:
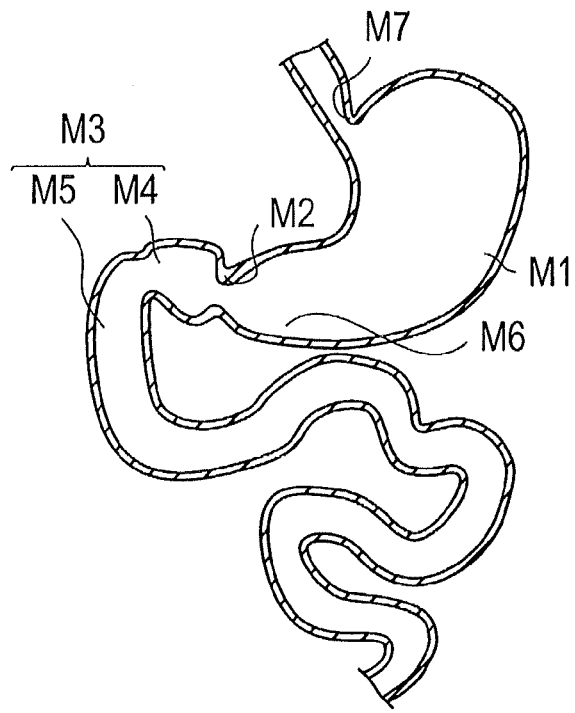
FIG. 6 is a schematic cross-sectional view that illustrates a part of the digestive tract.

The grasping device 40 grasps and moves the digestive tract device 100 to a predetermined position (desired position) and then releases the grasping to position the digestive tract device 100 at the predetermined position. An operation unit 42 which includes a lever 41 is provided on the operator side of the grasping device 40. By operating the lever 41, it is possible to grasp the digestive tract device 100 with a grasping member 43 provided on the tip of the grasping device 40 or release the grasping (refer to a dashed line in FIG. 5). The structure of the grasping device 40 is not particularly limited. In the illustrated example, the grasping device 40 includes a pair of diverging arms movably positioned inside a tube, wherein the arms are normally urged away from one another in the absence of an applied force, and are biased towards each other as the arms are pulled into the tube. The digestive tract device 100 is placed in a region near the pyloric ring M2 inside the digestive tract. As illustrated in FIG. 6, the pyloric ring M2 is located between the stomach M1 and the duodenum M3, and has a smaller inner diameter than the stomach M1 and the duodenum M3. The duodenum M3 has the duodenal bulb M4 which is adjacent to the stomach M1 with the pyloric ring M2 interposed therebetween and the pars descendens duodeni M5 which is located on the distal side of the duodenal bulb M4 and has a smaller inner diameter than the duodenal bulb M4. The stomach M1 contracts to be slim when it is empty, and expands to increase its diameter when food is taken in or ingested. Then, the ingested food is conveyed to the distal side while agitating the food by contracting waves of the stomach M1 and digesting the food with gastric juices into a degradation product in a chyme-like state. The pyloric antrum M6 secretes alkaline mucus to neutralize the acid degradation product in a chyme-like state. When the degradation product becomes alkaline, a sphincter muscle of the pyloric ring M2 loosens to open the pyloric ring M2, and the intestines move. Then, the degradation product is fed into the duodenum M3 through the pyloric ring M2 by the contraction of the pyloric antrum M6 located on the lower part of the stomach M1. The duodenum M3 conveys the degradation product to the distal side while agitating the degradation product by the movement of the intestines including the peristaltic movement, segmental movement, and pendular movement.

Figure 7:
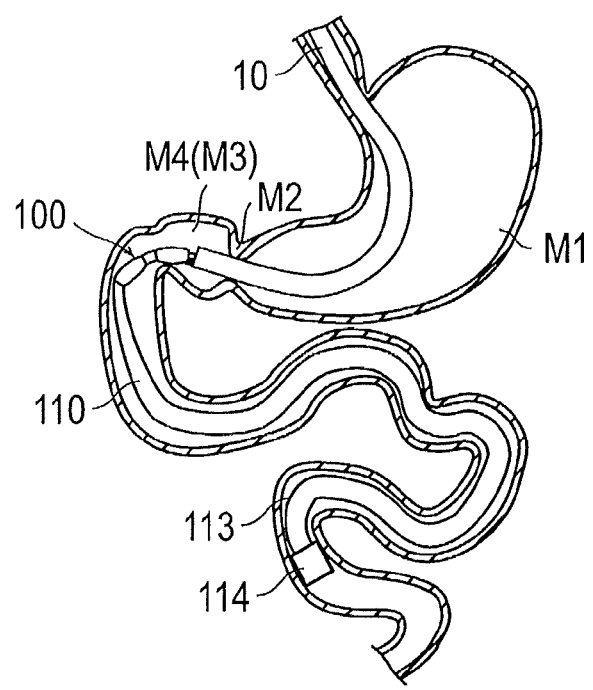
FIG. 7 is a schematic cross-sectional view that illustrates a state in which the digestive tract device is inserted into the digestive tract through an endoscope.

When placing the digestive tract device 100, the endoscope 10 is first inserted through the mouth or nose, and then moved forward until the tip of the endoscope 10 passes through the pyloric ring M2 while confirming an image as illustrated in FIG. 7. The tip of the endoscope 10 that has passed through the pyloric ring M2 is located inside the duodenum M3. The tip of the endoscope 10 may not necessarily pass through the pyloric ring M2 as long as the digestive tract device 100 can be inserted from the stomach M1 toward the duodenum M3 through the pyloric ring M2.

Then, the tubular portion 110 of the digestive tract device 100 is folded, the first expandable unit 130 and the second expandable unit 140 are contracted, and the inlet unit 160 is connected to the supply tube 32 continuous with, and in communication with, the pressure device 31 (refer to FIG. 5). Prior to the folding operation, the folded-back portion 114 is previously formed on the tubular portion 110, and the folded-back state is maintained by the holding unit 180. When folding the tubular portion 110, the entire body of the tubular portion 110 is folded in the longitudinal direction so as not to block the tip opening 112.

Then, the digestive tract device 100 is grasped by the grasping device 40, and inserted into the channel 12 of the endoscope 10. Further, the grasping device 40 is pushed to move the digestive tract device 100 to the tip side. The grasping device 40 and the digestive tract device 100 connected to the supply tube 32 may be previously inserted into the channel 12 before inserting the endoscope 10 through the mouth or nose.

Referring again to FIG. 7, the digestive tract device 100 is allowed to project inside the duodenum M3 from the tip of the endoscope 10 while confirming an image obtained by the endoscope 10, that is while confirming a distal position of the endoscope 10. After the distal position of the endoscope 10 is identified or determined, the digestive tract device 100 is introduced into the digestive tract through the channel of the endoscope 10. When the digestive tract device 100 reaches the duodenal bulb M4 adjacent to the pyloric ring M2 or the distal side with respect to the duodenal bulb M4, the folded tubular portion 110 extends to the distal side by the peristaltic movement of the duodenum M3. Further, in order to accelerate the extension of the tubular portion 110 by the peristaltic movement, an auxiliary member may be temporarily attached to the tip side of the tubular portion 110. The auxiliary member is, for example, a spherical member. The auxiliary member receives a force directing to the distal side by the peristaltic movement to allow the tubular portion 110 to extend. After the tubular portion 110 completely extends, the auxiliary member is detached from the tubular portion 110 by a force received from the peristaltic movement, and eventually discharged. When temporarily attaching the auxiliary member, an adhesive may be used, or the auxiliary member may be engaged with the tubular portion 110 so as to be detached therefrom with a predetermined force.

Figure 8:
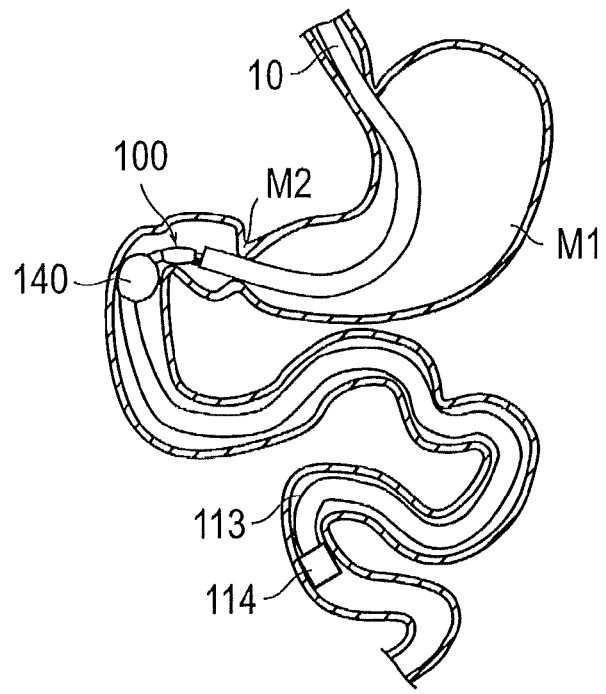
FIG. 8 is a schematic cross-sectional view that illustrates a state in which a second expandable unit of the digestive tract device inserted into the digestive tract is expanded.
Figure 9:
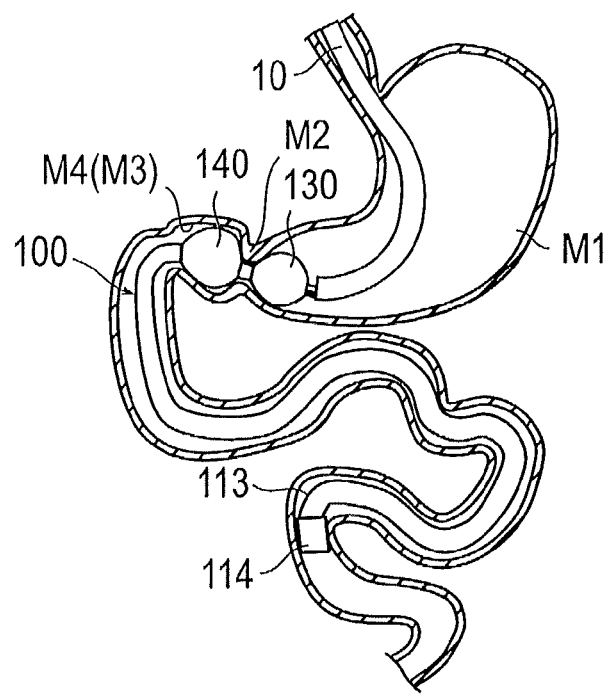
FIG. 9 is a schematic cross-sectional view that illustrates a state in which a first expandable unit of the digestive tract device inserted into the digestive tract is expanded.

Then, as illustrated in FIG. 8, fluid is supplied to the digestive tract device 100 by operating the pressure device 31. At this point, the pressure of the fluid is adjusted to a low (relatively low) pressure that is sufficient for the switching member 173 of the flow path switching unit 170 to block the first flow path 171 and maintain an open state of the second flow path 172 (refer to FIG. 3). Then, as illustrated in FIG. 9, the entire body of the digestive tract device 100 is moved back toward the proximal side by an operation at the hand. Then, the second expandable unit 140 and the first expandable unit 130 are expanded while confirming an image obtained by the endoscope 10, that is while identifying the position of the endoscope. Then, after the second expandable unit 140 is expanded up to a size that makes the second expandable unit 140 unable to pass through the pyloric ring M2, the pressure device 31 is operated to stop the supply of the fluid.

Accordingly, the first expandable unit 130 expanded to be larger than the inner diameter of the pyloric ring M2 is located on the proximal side with respect to the pyloric ring M2, and the second expandable unit 140 is fitted with the duodenal bulb M4. In addition, the pyloric ring M2 is sandwiched between the first expandable unit 130 and the second expandable unit 140. Therefore, the digestive tract device 100 is firmly retained in the digestive tract.

For example, there may also be performed a procedure in which the second expandable unit 140 is expanded to some extent, the digestive tract device 100 is then moved back to cause the second expandable unit 140 to make contact with the pyloric ring M2, and the second expandable unit 140 is then again expanded.

Thereafter, the supply tube 32 is pulled to detach the supply tube 32 from the inlet unit 160 of the digestive tract device 100. Because the backflow prevention unit 161 is provided in the digestive tract device 100, the fluid inside the digestive tract device 100 does not leak out and the first expandable unit 130 and the second expandable unit 140 are maintained in an expanded state even when the supply tube 32 is detached. Thereafter, the operation unit 42 of the grasping device 40 is operated to release the grasping of the digestive tract device 100 (refer to the dashed line in FIG. 5). Then, the endoscope 10, the grasping device 40, and the supply tube 32 are pulled out of the digestive tract and the procedure is completed.

Next, the action of the digestive tract device 100 according to the present embodiment will be described.

When a patient who has the digestive tract device 100 placed in the digestive tract takes or ingests food, the food is digested inside the stomach M1 and the degradation product in a chyme-like state then flows into the through hole 111 of the tubular portion 110 from the vicinity of the pyloric ring M2. At this time, the connection unit 150 located on the inner side of the pyloric ring M2 can be flexibly deformed, and therefore does not obstruct opening/closing of the pyloric ring M2. Further, because the tubular portion 110 can be flexibly deformed in response to the movement of the digestive tract, the degradation product flowing into the tubular portion 110 is pushed out toward the distal side while being agitated by the movement of the duodenum M3. Further, nutrients do not directly make contact with the duodenum M3 and the upper part of the jejunum both located on the upper part of the small intestine and covered by the tubular portion 110, and the nutrient are absorbed after the food passes through the tubular portion 110. When the food does not make contact with the upper part of the small intestine, the absorption of nutrients is reduced, and GIP, glucagon and the like which are gastrointestinal hormones secreted in response to the stimulus of nutrients become difficult to secrete. GIP and glucagon are considered factors which reduce the secretion of insulin. Therefore, when GIP and glucagon are not secreted, the secretion of insulin is not obstructed, and the blood sugar level can be reduced by insulin. Then, when the undigested food reaches the lower part of the jejunum and the ileum both located on the lower part of the small intestine, the secretion of GLP-1 which is a gastrointestinal hormone considered as a factor which accelerates the secretion of insulin increases in response to the stimulus of nutrients. As a result, further acceleration of the secretion of insulin makes it possible to reduce the blood sugar level. Placing the digestive tract device 100 inside the digestive tract in this manner reduces the digestion and absorption of nutrients and reduces the blood sugar level. As a result, a high effect is exhibited on the treatment of diabetes (especially type 2 diabetes) and obesity.

The digestive tract device disclosed here has useful application to diabetes and obesity, including treating, healing, relieving, easing, changing, improving, modifying, recovering, making better, or acting on diseases or symptoms of the patients.

A specific region in which the first expandable unit 130 and the second expandable unit 140 are retained preferably has a smaller inner diameter than regions on the proximal side and the distal side of such specific region, and is the pyloric ring M2 in the present embodiment. However, as described below, for example, the first expandable unit 130 and the second expandable unit 140 may be placed on the cardia M7 (refer to FIG. 21) on the upper part of the stomach M1, or another region inside the digestive tract.

The digestive tract device 100 having the above configuration makes it possible to rather easily adjust the length of the tubular portion 110 by releasing the holding of the tubular portion 110 by the holding unit 180 or changing the position of the tubular portion 110 held by the holding unit 180 after introducing the tubular portion 110 into a living body. Therefore, when increasing/reducing the digestion and absorption of nutrients in the stomach and the small intestine, it is not necessary to perform a complicated operation of replacing the tubular portion 110. Therefore, it is possible to rather easily adjust the length of the tubular portion 110 after the placement and reduce the burden on a living body associated with the length adjustment.

Further, when the holding unit 180 holds the tubular portion 110 in a folded-back state with the tip opening 112 open, it is possible to extend the tubular portion 110 in the longitudinal direction by a relatively simple operation of pulling the folded-back portion 114 after the placement or along with a decrease in the holding power or holding strength with the passage of time after the placement. Therefore, it is not necessary to perform an operation of temporarily taking out the tubular portion 110 from the small intestine and introducing another tubular portion having a different length into the small intestine when adjusting the length of the tubular portion 110 to be longer after the placement. Thus, it is possible to reduce the burden on a living body associated with the adjustment of the length of the tubular portion 110 retained inside the living body. Further, because the holding unit 180 holds the folded-back portion 114 in a folded state with the tip opening 112 of the tubular portion 110 open without blocking the tip opening 112, it is not necessary to perform an operation of opening the tip of the tubular portion 110 inside a living body when using the digestive tract device 100. Therefore, a preparatory operation from when the digestive tract device 100 is introduced into a living body until when the digestive tract device 100 is made usable can be performed in a relatively simple manner.

Further, the holding unit 180 includes at least the first holding regions 181, 182 and the second holding regions 183, 184 having different holding powers or holding strengths for holding the folded-back portion 114 in a folded-back state. Further, the first holding regions 181, 182 are arranged on the base end side with respect to the second holding regions 183, 184, and have a larger holding power or holding strength than the second holding regions 183, 184. Therefore, when introducing and placing the digestive tract device 100 inside the living body, it is possible to prevent the tubular portion 110 from carelessly extending because of a decrease in the holding power or holding strength of the holding unit 180 caused by contact with the living body.

When the holding unit 180 includes a thermally-fused portion to which the folded-back portion 114 is bonded by thermal fusion, the holding unit 180 can be formed on the tubular portion by a relatively simple method using thermal fusion. In addition, it is also possible to rather easily adjust the holding power or holding strength in the holding unit 180.

When the tip end 115 of the main body 113 continuous with the folded-back portion 114 is arranged on the tip side of the tubular portion 110 with respect to the tip-side folding back position P1 of the folded-back portion 114 when the holding unit 180 holds the folded-back portion 114, it is possible to reduce the length of the tubular portion 110 while maintaining the folded-back portion 114 in a folded-back state by the holding unit 180 by cutting the surplus portion 116 of the main body 113. Accordingly, the digestive tract device 100 is provided with a length adjustment mechanism for extending the length of the tubular portion 110 which includes the folded-back portion 114 and the holding unit 180 and a length adjustment mechanism that makes it possible to reduce the length of the tubular portion 110 by performing an operation such as cutting. Therefore, it is possible to adjust the length of the tubular portion 110 to be longer or shorter within a predetermined range after introducing the tubular portion 110 into a living body. Thus, it is possible to provide the digestive tract device 100 capable of further improving the flexibility of procedures.

Further, when the length L1 between the tip-side folding back position P1 of the folded-back portion 114 and the tip end 115 of the main body 113 is longer than the length L2 between the tip-side folding back position P1 of the folded-back portion 114 and the retention unit 140, the length between the tip-side folding back position P1 of the folded-back portion 114 and the tip end 115 of the main body 113 is relatively long. Therefore, a relatively long length of the surplus portion 116 which enables the length adjustment can be ensured. As a result, it is possible to provide the digestive tract device 100 with better usability.

Further, because the retention unit 120 is provided on the base end side in the penetration direction of the tubular portion 110, the digestive tract device 100 can be held to a living body in a region located on the upstream side of the flow of an introduced object such as food with respect to the duodenum. Therefore, it is possible to reliably prevent the occurrence of detachment even when retaining the digestive tract device 100 for a relatively long period of time.

In the embodiment described above, there has been described the configuration in which the holding unit 180 includes a plurality of holding regions such as the first holding regions 181, 182 and the second holding regions 183, 184. However, the number of holding regions provided in a single holding unit is not particularly limited as long as at least one or more holding regions are provided. Therefore, it is possible to increase the number of holding regions to two or more depending on the length of the folded-back portion 114 and the like.

<Modification>

Figure 10:
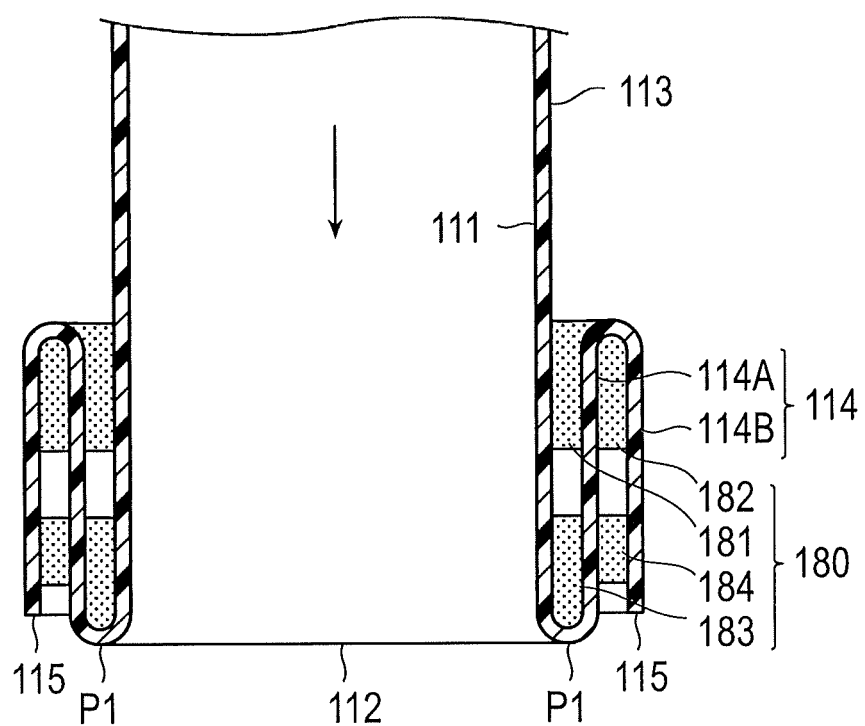
FIG. 10 is an enlarged cross-sectional view that illustrates a folded-back portion and the vicinity of the folded-back portion according to a modification of the first embodiment.

FIG. 10 is a partial cross-sectional view that illustrates a modification of the above first embodiment. In the modification, when the holding unit 180 holds the folded-back portion 114, the tip end 115 of the main body 113 continuous with the folded-back portion 114 is arranged on the base end side of the tubular portion 110 with respect to the tip-side folding back position P1 of the folded-back portion 114. In the above embodiment, the surplus portion 116 is formed on the main body 113 because the tip end 115 of the main body 113 is arranged on the tip side with respect to the folding back position P1. However, the surplus portion 116 is not formed on the main body 113 described in the modification. In the digestive tract device 100 having such a configuration, it is not possible to perform an operation of reducing the length of the tubular portion 110 by cutting the surplus portion 116. However, a decrease in the holding power of the holding unit 180 caused by contact between the surplus portion 116 and the living body is not caused when introducing the tubular portion 110 into a living body. Therefore, it is possible to more effectively prevent careless extension of the tubular portion 110 caused by a decrease in the holding power or holding strength of the holding unit 180 than the case in which the surplus portion 116 is formed.

Second Embodiment

Figure 11:
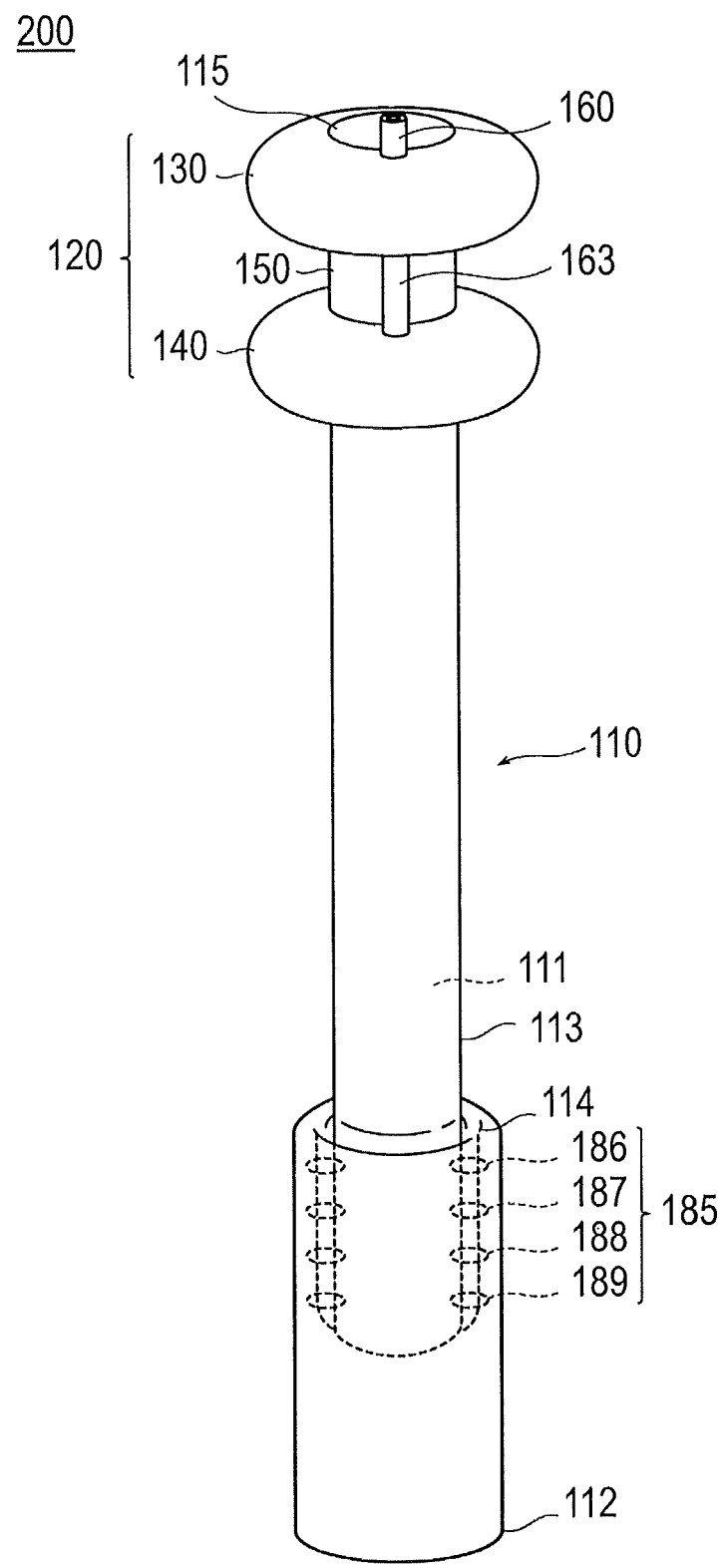
FIG. 11 is a perspective view that illustrates a digestive tract device according to a second embodiment representing another example of the digestive tract device disclosed here.

FIG. 11 is a perspective view that illustrates a digestive tract device 200 according to a second embodiment representing another example of the digestive tract device disclosed here. Although the digestive tract device 100 according to the first embodiment is provided with the holding unit 180 which is formed by thermally fusing the folded-back portion 114, the configuration of the holding unit is not limited thereto. For example, as illustrated in FIG. 11, a holding unit 185 can include biocompatible threads 186, 187, 188, 189 which are dissolved by a digestive juice or the like secreted inside a living body. For example, hydroxypropyl methylcellulose phthalate which is an enteric material can be used as the material of the threads.

As illustrated in FIG. 11, for example, a folded-back portion 114 of a tubular portion 110 can be held in a folded-back state by suturing the folded-back portion 114 at different positions in the longitudinal direction using these threads. Although the number of positions to be sutured is not particularly limited, for example, the folded-back portion 114 can be sutured at four different positions in the longitudinal direction as illustrated. Further, the thread that is located closest to the base end preferably has a stronger holding power than the other threads 187, 188, 189 so as to prevent the holding from being released when introducing the tubular portion 110 into a living body.

As with the digestive tract device 100 according to the above first embodiment, it is possible to reduce the burden on a living body associated with the adjustment of the length of the tubular portion 110 retained inside a living body also in the digestive tract device 200 according to the present embodiment. Further, the holding unit 185 holds the folded-back portion 114 in a folded state with a tip opening 112 of the tubular portion 110 open without blocking the tip opening 112. Therefore, it is not necessary to perform an operation of opening the tip of the tubular portion 110 inside a living body when using the digestive tract device 110. Thus, a preparatory operation from when the digestive tract device 100 is introduced into a living body until when the digestive tract device 100 is made usable can be performed in a relatively simple manner. Further, when the holding unit 185 has the biocompatible threads for suturing the folded-back portion 114, it is possible to extend the tubular portion 110 by a relatively simple operation of pulling each of the threads or with the lapse of time after the placement.

Although there have been described the first embodiment in which the holding unit 180 includes the thermally-fused portion and the second embodiment in which the holding unit 185 includes the biocompatible threads, it is only required that the holding unit have at least a function capable of holding the folded-back portion 114 in a folded-back state and releasing the holding. Therefore, for example, the holding unit may be configured using both the thermally-fused portion and the threads, or using another member capable of physically or chemically holding the folded-back portion 114.

Further, although there has been described the embodiment in which the folded-back portion 114 is formed on the outer side of the tubular portion 110 by folding back the main body 113 of the tubular portion 110, for example, the folded-back portion 114 can also be formed on the inner side of the tubular portion 110 by folding back the main body 113.

Third Embodiment

Next, a digestive tract device 400 according to a third embodiment will be described. The digestive tract device 400 according to the third embodiment differs from each of the digestive tract devices according to the above embodiments in the configuration of a holding unit.

First, the main configuration of the digestive tract device 400 will be described with reference to FIGS. 12 to 15. Description for the components already described in the first embodiment will be partially omitted.

Figure 12:
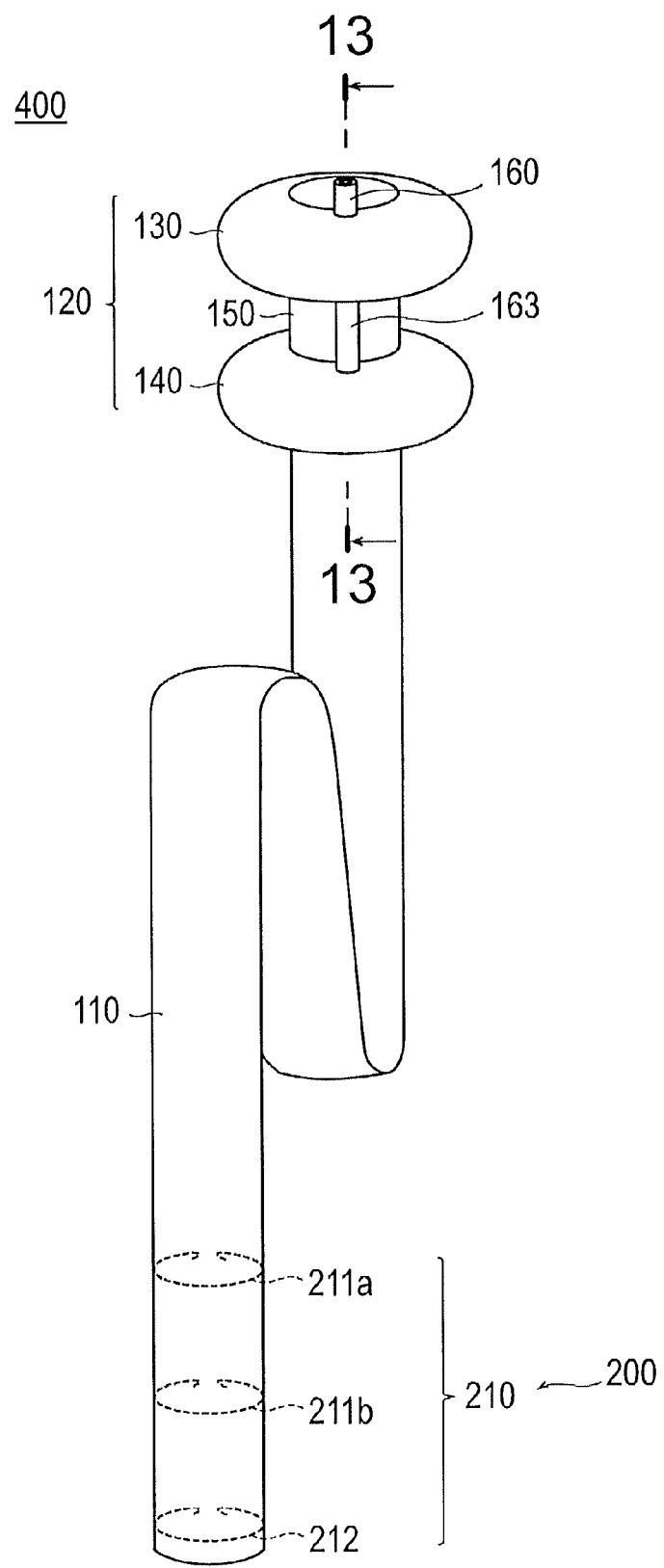
FIG. 12 is a perspective view that illustrates a digestive tract device according to a third embodiment representing another example of the digestive tract device disclosed here.
Figure 13:
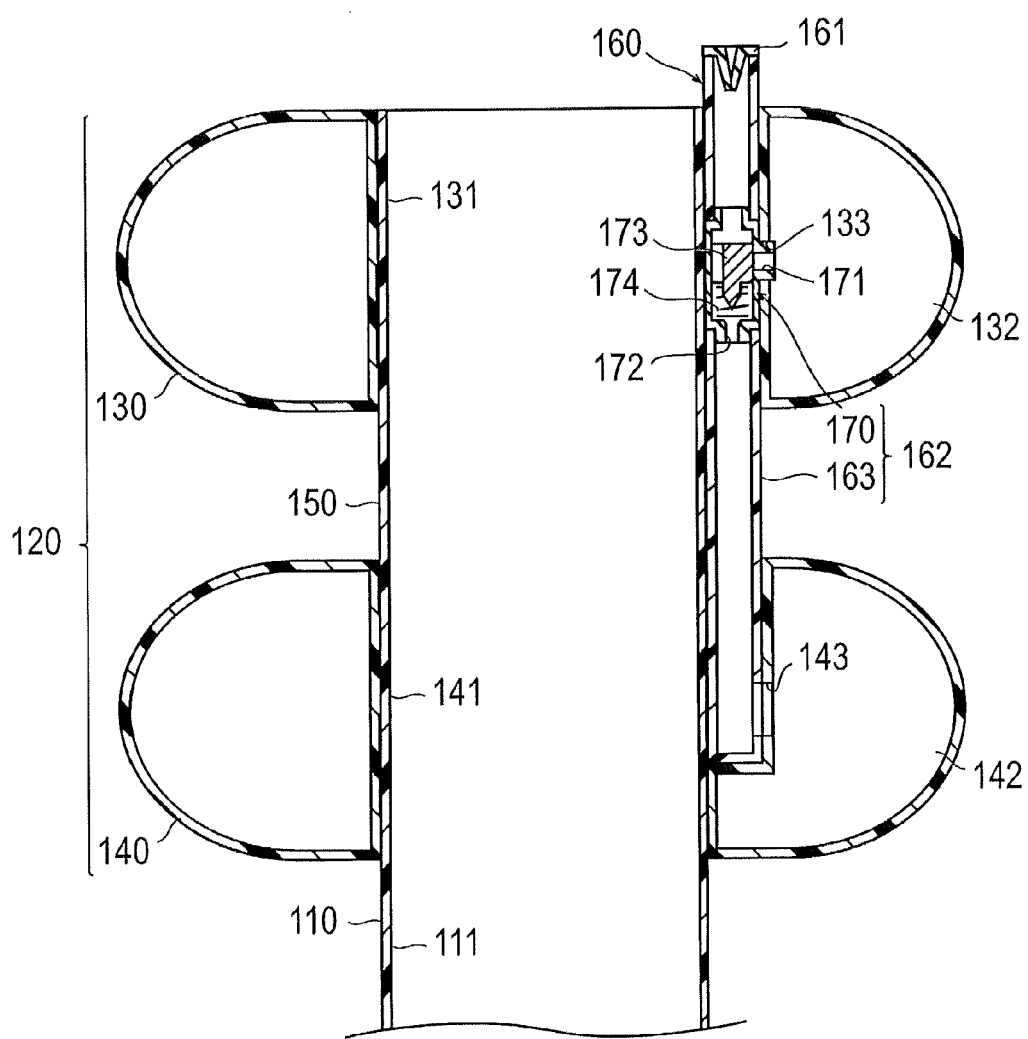
FIG. 13 is a cross-sectional view taken along the section line 13-13 of FIG. 12.

As illustrated in FIGS. 12 and 13, the digestive tract device 400 is provided with a flexible tubular portion 110 which is formed in a tubular shape and has a through hole 111, a retention unit 120 which is provided on one end in the penetration direction of the tubular portion 110 and holds the tubular portion 110 inside a living body, and a length adjustment unit 200 for adjusting the length of the tubular portion 110.

The retention unit 120 is provided with a first expandable unit 130 and a second expandable unit 140 which are arranged along the penetration direction (axial direction) of the tubular portion 110, a connection unit 150 which connects the first expandable unit 130 and the second expandable unit 140 to each other, and an inlet unit 160 which allows fluid to flow into the first expandable unit 130 and the second expandable unit 140.

Next, the length adjustment unit 200 provided in the digestive tract device 400 will be described.

Referring to FIGS. 14A, 14B, and 15A to 15C, the length adjustment unit 200 includes a holding unit 210 which is provided in the tubular portion 110. The holding unit 210 has a configuration capable of holding at least a part of the tubular portion 110 in a lifted state toward the base end side of the tubular portion 110.

The holding unit 210 includes a plurality of locking pieces 211a, 211b, 212 which can be freely engaged with and disengaged from each other. More specifically, the holding unit 210 includes the two first locking pieces 211a, 211b and the single second locking piece 212. Although the locking pieces are referred to as the first locking pieces and the second locking piece for descriptive purposes, a second locking piece refers to a locking piece that is arranged on the tip side of the tubular portion with respect to another locking piece. Therefore, for example, in the relationship with the first locking piece 211a that is located closest to the base end, the intermediately located first locking piece 211b may also be referred to as the second locking piece.

The locking pieces 211a, 211b, 212 are arranged in the longitudinal direction of the tubular portion 110 so as to be separated from each other. The distance between the locking pieces 211a, 211b, 212 is not limited, and can be set to any distance. Further, the attaching positions and the number of the locking pieces 211a, 211b, 212 are not limited to those illustrated in the drawings, and can be appropriately changed.

The locking pieces 211a, 211b, 212 have the same configuration. Therefore, the configuration of the second locking piece 212 illustrated in FIGS. 14A and 14B will be described, and a detailed description for the other locking pieces will not be repeated because the description is the same. A configuration is the same in all of the locking pieces.

The second locking piece 212 includes an elastically deformable ring-shaped member which has an insertion hole 217 formed on the center thereof. Although the material of the second locking piece 212 is not particularly limited, for example, a metal material and a resin material can be used.

Figure 14A:
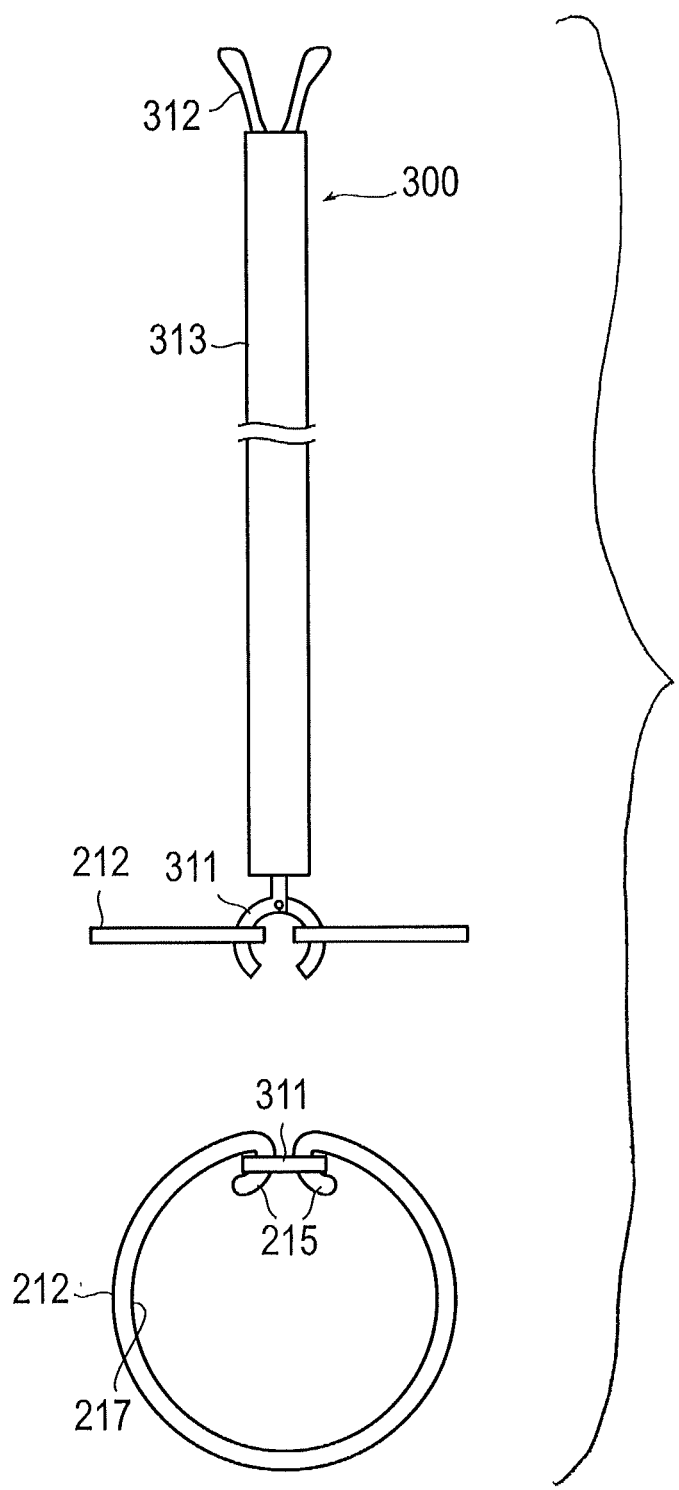
FIG. 14A is a diagram explaining a locking piece provided in a holding unit, specifically, a diagram that illustrates the locking piece before being deformed.
Figure 14B:
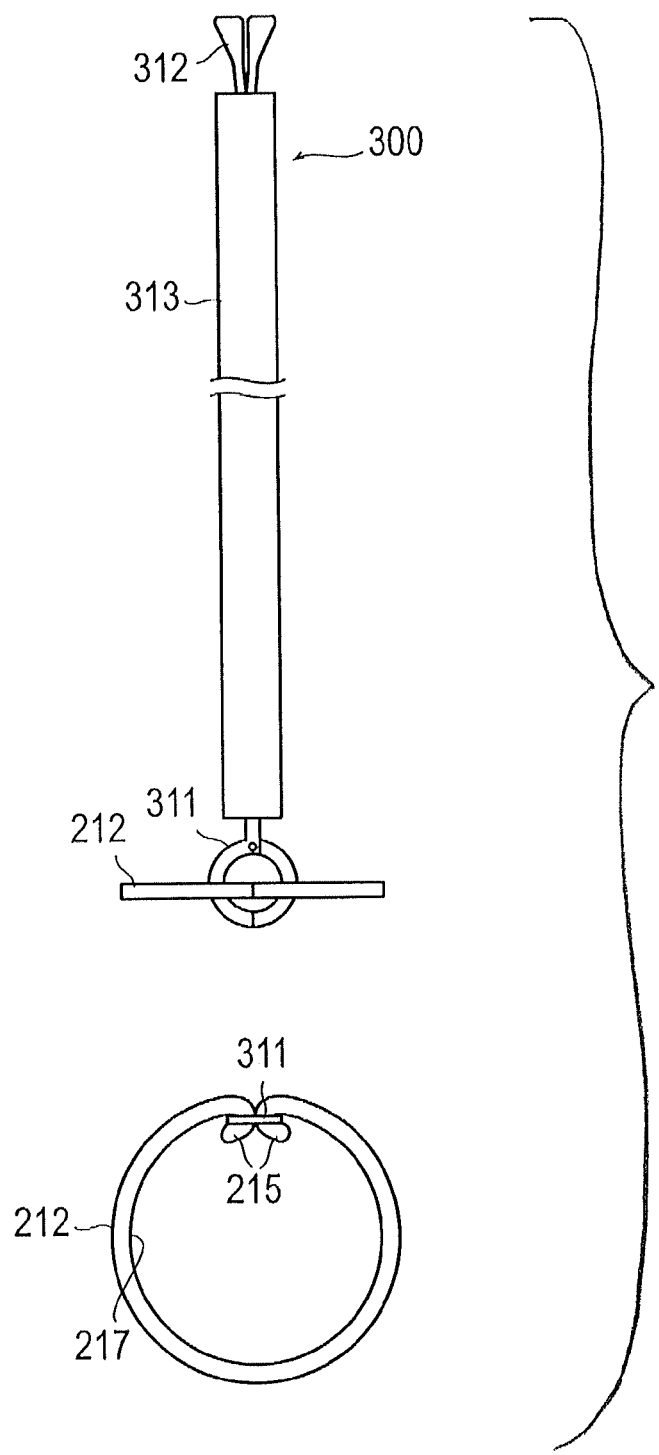
FIG. 14B is a diagram or explaining the locking piece provided in the holding unit, specifically, a diagram that illustrates the locking piece after being deformed.

The second locking piece 212 is provided with a squeezing unit 215 which is provided for reducing the diameter of the second locking piece 212. As illustrated in FIGS. 14A and 14B, the outer diameter (and inner diameter) of the second locking piece 212 can be reduced by grasping the squeezing unit 215 using a predetermined squeezing tool 300. The shape of the squeezing unit 215 is not limited to the illustrated shape as long as it can be grasped with the squeezing tool 300 or the like.

A known tool such as a forceps and a snare can be used as the squeezing tool 300 for reducing the outer diameter (and inner diameter) of the second locking piece 212. For example, a tool that is provided with an openable/closable tip arm 311, a hand-side operation unit 312 for operating an opening/closing operation of the tip arm 311, and an elongated flexible main body 313 as illustrated is used as the squeezing tool 300. The tip arm 311 can be closed by virtue of an operator grasping the hand-side operation unit 312. When the tip arm 311 is closed, the squeezing unit 215 of the second locking piece 212 is squeezed, and the outer diameter (and inner diameter) of the second locking piece 212 is reduced. Further, the tip arm 311 can be opened by virtue of the operator releasing the grasping of the hand-side operation unit 312. When the tip arm 311 is opened, the grasped state of the squeezing unit 215 of the second locking piece 212 is released, and the second locking piece 212 is returned to its original shape.

The second locking piece 212 is fixed to the inner surface of the through hole 111 of the tubular portion 110. The fixation is performed by fusing or bonding a part of the outer peripheral surface of the second locking piece 212 to the inner surface of the through hole 111. The squeezing unit 215 is not fixed to the tubular portion 110 so that the second locking piece 212 can be deformed to have a reduced diameter and returned to its original shape.

The insertion hole 217 formed on the second locking piece 212 can be arranged so as to communicate with the through hole 111 formed on the tubular portion 110. Such arrangement makes it possible to allow an introduced object such as food to smoothly flow down inside the tubular portion 110 regardless of the placement of the second locking piece 212.

Next, a method for adjusting the length of the tubular portion 110 will be described.

Figure 15A:
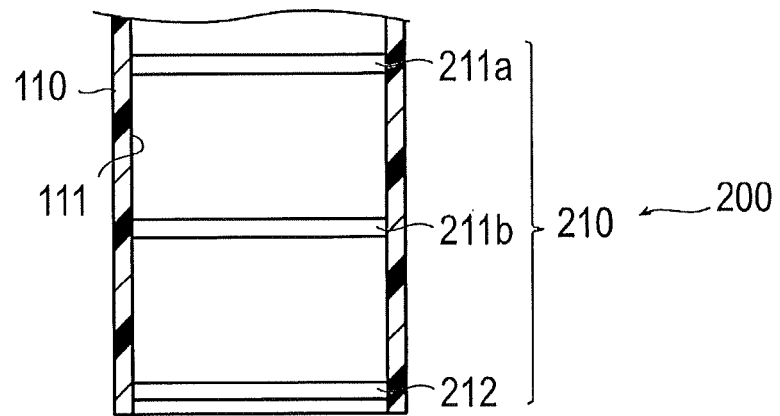
FIG. 15A is a diagram explaining a method for adjusting the length of a tubular portion, specifically, a cross-sectional view that illustrates the tubular portion before the length of the tubular portion is adjusted.

As illustrated in FIG. 15A, the plurality of locking pieces 211a, 211b, 212 are previously attached to the tubular portion 110.

Figure 15B:
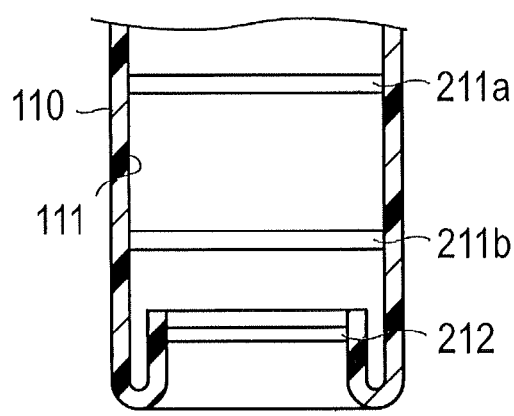
FIG. 15B is a diagram explaining the method for adjusting the length of the tubular portion, specifically, a cross-sectional view that illustrates a state in which the locking piece is deformed in the length adjustment.

As illustrated in FIG. 15B, the diameter of the second locking piece 212 is reduced using the squeezing tool 300 to allow the second locking piece 212 to pass through the insertion hole 217 of the first locking piece 211b so as to be lifted toward the base end side. The second locking piece 212 can be located on the base end side with respect to the first locking piece 211b by this operation.

Figure 15C:
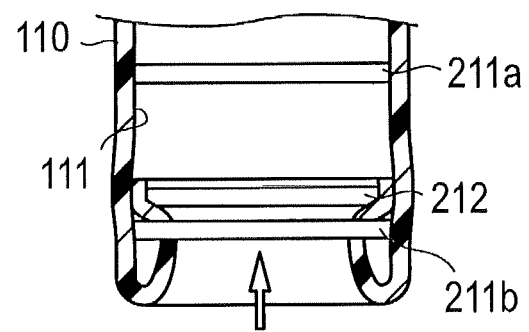
FIG. 15C is a diagram explaining the method for adjusting the length of the tubular portion, specifically, a cross-sectional view that illustrates a state after adjusting the length using the locking piece.

As illustrated in FIG. 15c, the grasping of the squeezing unit 215 of the second locking piece 212 by the squeezing tool 300 is released to return the second locking piece 212 to its original state. The second locking piece 212 is locked to the end face on the base end side of the first locking piece 211b by this operation, and the length of the tubular portion is therefore reduced. During when the second locking piece 212 is locked to the first locking piece 211b, a part of the tubular portion 110 is held in a lifted state toward the base end side. In order to perform the length adjustment, it is only required that at least a part of the second locking piece 212 be locked to the first locking piece 211b.

When adjusting the length of the tubular portion 110 to be further shorter, an operation of deforming the second locking piece 212 to have a reduced diameter to allow the second locking piece 212 to pass through the insertion hole 217 of the first locking piece 211a located on the base end side is performed. Further, when returning the length to its original length, it is only necessary to deform the second locking piece 212 to have a reduced diameter to allow the second locking piece 212 to pass through the insertion hole 217 of the first locking piece 211b and move to the tip side. Further, it is also possible to perform the length adjustment by locking the first locking piece 211b located on the middle to the first locking piece 211a located on the base end side without using the second locking piece 212. As described above, in the digestive tract device 400, the reversible length adjustment for reducing or increasing the length of the tubular portion 110 can be performed by a relatively simple operation of deforming the second locking piece 212 from a predetermined initial shape (first shape) to a reduced-diameter shape (second shape) and moving the deformed second locking piece 212 along the longitudinal direction of the tubular portion 110.

The outer diameter of the second locking piece 212 located on the tip side of the tubular portion 110 is preferably smaller than the outer diameter of the first locking piece 211b because such a configuration makes it possible to more reliably lock the second locking piece 212 to the first locking piece 211b. Similarly, the outer diameter of the intermediately located first locking piece 211b is preferably larger than the outer diameter of the first locking piece 211a located on the base end side.

Next, a method for placing the digestive tract device 400 inside the digestive tract will be described.

Figure 16:
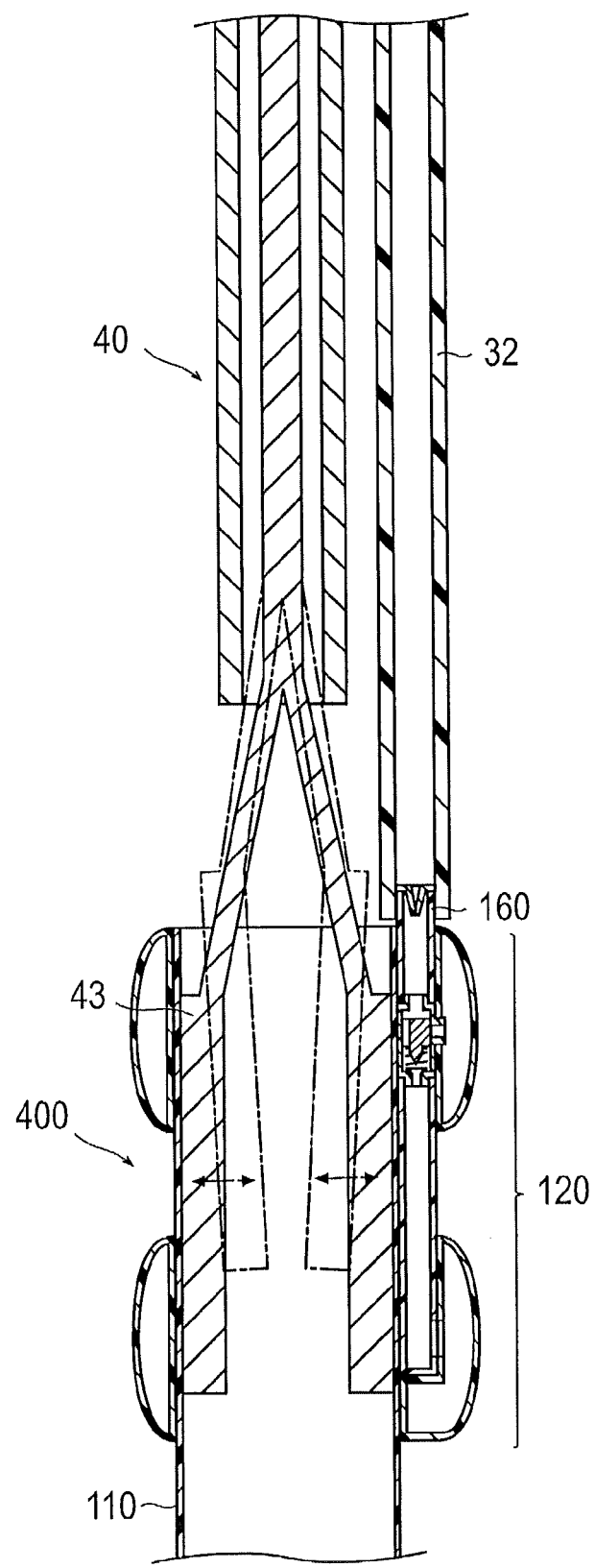
FIG. 16 is a cross-sectional view that illustrates a state in which a grasping member and a supply tube are connected to the digestive tract device according to the third embodiment.

The placement of the digestive tract device 400 can be performed using the digestive tract device placing system described above as illustrated in FIG. 16 (refer to FIG. 4). Further, a retention operation using the first expandable unit 130 and the second expandable unit 140 is also the same as that in the first embodiment. Therefore, a detailed description of those aspects of the method which have already been described above will not be repeated.

Figure 17:
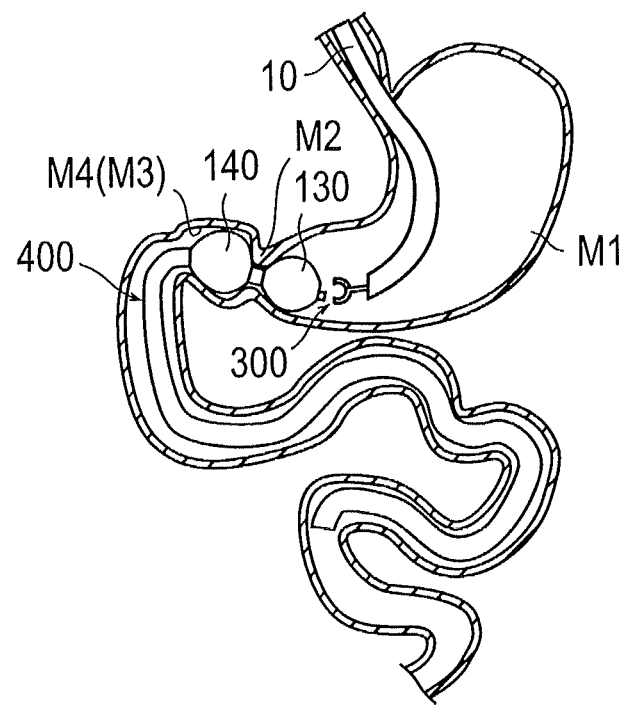
FIG. 17 is a schematic cross-sectional view that illustrates a state in which a device for length adjustment is inserted into the digestive tract.

When adjusting the length of the tubular portion 110 after placing the digestive tract device 400, the endoscope 10 is introduced into a living body as illustrated in FIG. 17. Then, the squeezing tool 300 is introduced into the living body through the channel 12 of the endoscope 10. Then, the length of the tubular portion is adjusted using the locking pieces 211a, 211b, 212 while confirming an image obtained by the endoscope 10.

As described above, the digestive tract device 400 according to the present embodiment can reduce the length of the tubular portion 110 by holding at least a part of the tubular portion 110 in a lifted state toward the base end side by the holding unit 210 provided in the length adjustment unit 200. Further, the length of the tubular portion 110 can be returned to its original shape by releasing the holding by the holding unit 210. Therefore, it is possible to reversibly adjust the length of the tubular portion 110 after the digestive tract device 400 is placed in a living body.

When the holding unit 210 includes the first locking pieces 211a, 211b which are attached to the tubular portion 110 and the second locking piece 212 which is attached to the tubular portion 110 on the tip side with respect to the first locking pieces 211a, 211b and can be freely engaged with and disengaged from the first locking pieces 211a, 211b, it is possible to reduce the length of the tubular portion 110 by a relatively simple operation of locking the first locking pieces 211a, 211b and the second locking piece 212 to each other. Further, it is possible to return the length of the tubular portion 110 to its original length by a rather simple operation of releasing the locking between the first locking pieces 211a, 211b and the second locking piece 212.

When the second locking piece 212 is freely deformable between the first shape that enables the second locking piece 212 to move to the base end side of the tubular portion 210 beyond the first locking pieces 211a, 211b and the second shape that enables at least a part of the second locking piece 212 to be locked to the first locking pieces 211a, 211b on the base end side with respect to the first locking pieces 211a, 211b, it is possible to adjust the length of the tubular portion 110 by a relatively simple operation of moving the second locking piece 212 deformed in the second shape to a position on the base end side with respect to the first locking pieces 211a, 211b.

When the insertion holes 217 through which an introduced object such as food can pass are formed on the first locking pieces 211a, 211b and the second locking piece 212 and the second locking piece 212 is freely deformable to the second shape that enables the second locking piece 212 to be inserted through the insertion holes 217 of the first locking pieces 211a, 211b, it is possible to allow an introduced object such as food to smoothly flow down inside the tubular portion 110 regardless of the placement of the first locking pieces 211a, 211b and the second locking piece 212.

When the plurality of first locking pieces 211a, 211b are arranged in the longitudinal direction of the tubular portion 110 so as to be separated from each other, the length of the tubular portion 110 can be adjusted in a multistage manner. As a result, it is possible to provide the digestive tract device 400 with more improved usability.

When the second locking piece 212 is composed of an elastic member that is deformable between the first shape and the second shape, the second locking piece 212 can be locked to the first locking pieces 211a, 211b by elastically deforming the second locking piece 212. Therefore, an operation required for the length adjustment can be more easily performed.

The retention unit 120 can be modified as long as it can hold the tubular portion inside a living body. For example, a retention unit which is composed of a single balloon or a stent type retention unit which is locked to a living body can also be employed. The same is true of the digestive tract devices 100, 200 according to the first embodiment.

The member constituting each of the locking pieces is not limited to an elastically deformable member. For example, a plastically deformable member can also be used. When each of the locking pieces is composed of a plastically deformable member, it is possible to adjust the length of the tubular portion 110 to be shorter, for example, by squeezing the locking piece using a squeezing tool or the like so as to be plastically deformed, lifting the plastically-deformed locking piece toward the base end side, and allowing the lifted locking piece to be locked thereto. The locked state can be released by plastically deforming the locking piece so as to return to its original shape. The other procedures in the length adjustment can be performed in the same manner as in the case in which an elastic member is used as the locking piece.

<Modifications>

Next, modifications of the above third embodiment will be described.

Figure 18A:
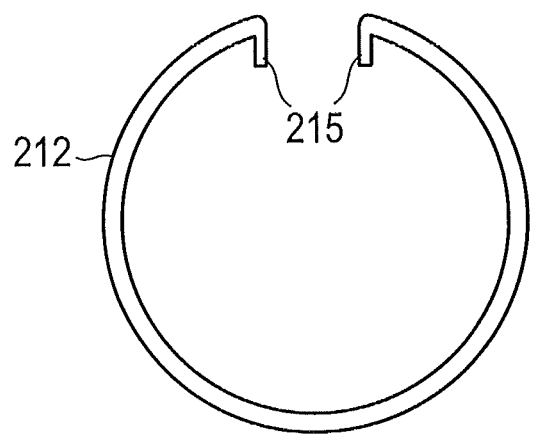
FIG. 18A is a diagram explaining a modification of a length adjustment unit.

FIG. 18A illustrates a locking piece 212 which is provided with a squeezing unit 215 having a different shape from the squeezing unit of the above embodiment. The squeezing unit 215 can be formed, for example, in a linear shape as illustrated. Also when the squeezing unit 215 is formed in such a shape, the diameter of the locking piece 212 can be reduced by grasping the squeezing unit 215.

Figure 18B:
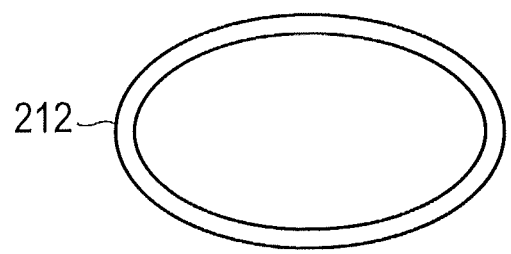
FIG. 18B is a diagram explaining a modification of the length adjustment unit.
Figure 18C:
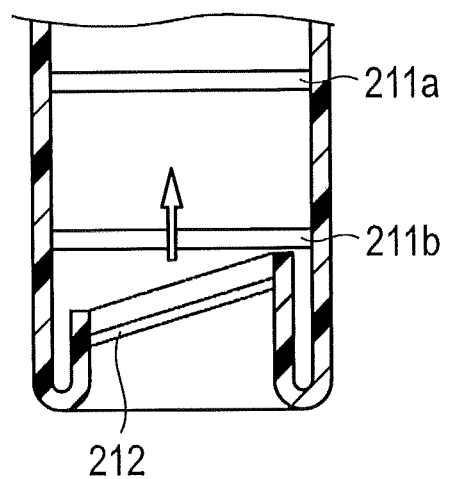
FIG. 18C is a diagram explaining a modification of the length adjustment unit.

FIG. 18B illustrates a locking piece 212 which can be locked without performing an operation of deforming the locking piece 212 to have a reduced diameter. For example, when using the locking piece 212 having an elliptical shape as illustrated, it is possible to allow the locking piece 212 to pass through the insertion holes 217 of the locking pieces 211a, 211b by inclining the locking piece 212 as illustrated in FIG. 18C. The locking piece 212 and the locking pieces 211a, 211b can be locked to each other by mounting the locking piece 212 on the locking pieces 211a, 211b in a parallel state after the locking piece 212 passes through the insertion holes 217.

Figure 19A:
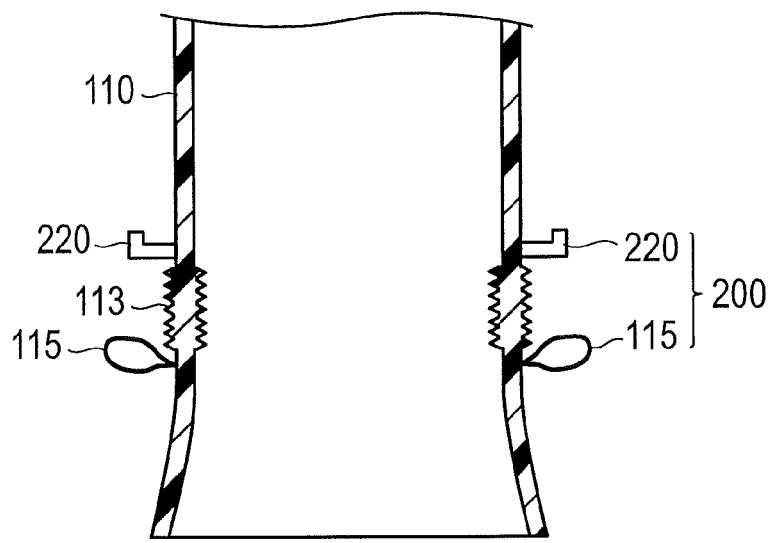
FIG. 19A is a diagram explaining a modification of the length adjustment unit.
Figure 19B:
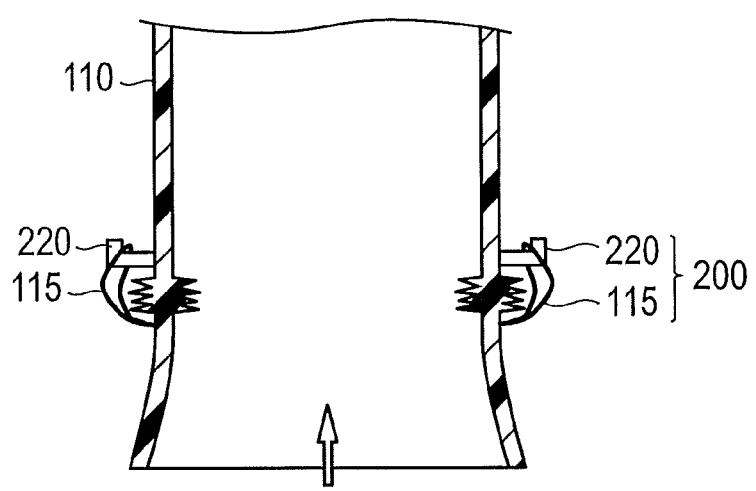
FIG. 19B is a diagram explaining a modification of the length adjustment unit.

FIG. 19A illustrates a digestive tract device which can perform the length adjustment using a holding unit 200 provided on the outer side of the tubular portion 110. For example, as illustrated, the holding unit 200 includes a ring-shaped string 115 and a projection 220 which are both provided on the outer side of the tubular portion 110. As illustrated in FIG. 19B, the length of the tubular portion 110 can be adjusted by hooking the string 115 on a holding unit 210. In order to perform smooth lifting toward the base end side of the tubular portion 110, bellows-like creases 113 may be formed on a part of the tubular portion 110 or the tip part of the tubular portion 120 may be formed in a tapered shape.

Figure 20A:
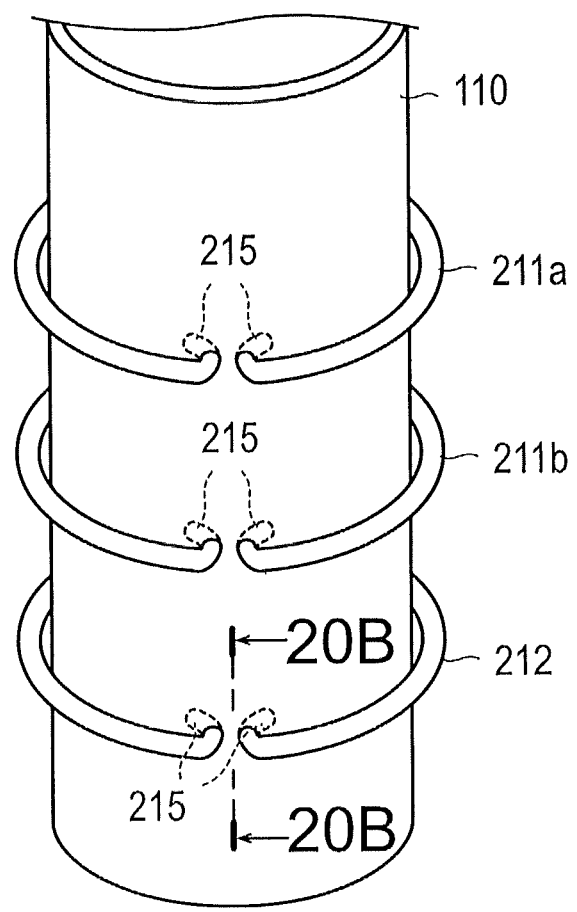
FIG. 20A is a diagram explaining a modification of the length adjustment unit, specifically, a perspective view that illustrates the appearance of the tubular portion.
Figure 20B:
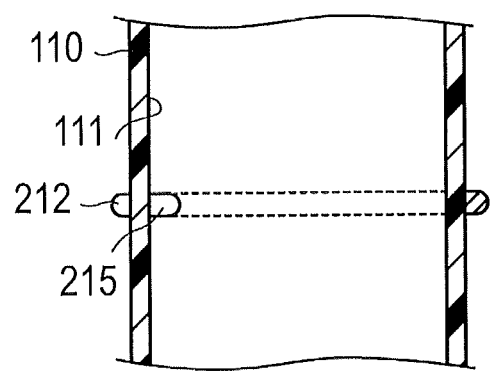
FIG. 20B is a diagram explaining a modification of the length adjustment unit, specifically, a cross-sectional view taken along the section line 20B-20B of FIG. 20A.

FIG. 20A illustrates a digestive tract device which is provided with ring-shaped locking pieces 211a, 211b, and 212 each of which has a squeezing unit 215 arranged on the inner side of the tubular portion 110 and the other regions fixed to the outer side of the tubular portion 110. FIG. 20B illustrates a partial cross-sectional view of the tubular portion 110. Also in such a form, the locking piece 212 can be deformed to have a reduced diameter by grasping the squeezing unit 215 of the locking piece 212 from the inner side of the tubular portion 110. Then, the locking piece 212 deformed to have a reduced diameter is lifted toward the base end side and locked to the locking pieces 211a, 211b, so that the length of the tubular portion 110 can be adjusted to be shorter. Also in such a form in which each of the locking pieces 211a, 211b, 212 is partially arranged on the inner side and the outer side of the tubular portion 110, a function for adjusting the length of the tubular portion 110 can be applied to the digestive tract device.

As described in each of the modifications, the digestive tract device according to the present embodiment can be variously modified as long as it is provided with a holding unit capable of reducing the length of the tubular portion by holding at least a part of the tubular portion in a lifted state toward the base end side of the tubular portion and returning the length of the tubular portion to its original length by releasing the lifted state of the tubular portion.

<Alternative Retention Position>

Figure 21:
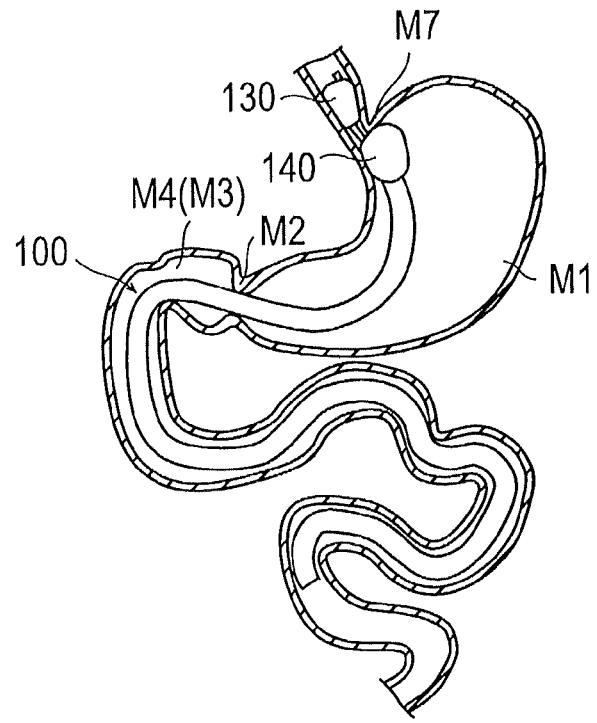
FIG. 21 is a cross-sectional view that illustrates an alternation of the position of retaining the digestive tract device.

FIG. 21 illustrates an alternative of the retention position of the digestive tract device. In each of the above embodiments, the pyloric ring M2 is sandwiched between the first expandable unit 130 and the second expandable unit 140 which are both expanded near the pyloric ring M2 to retain the digestive tract device 100 inside a living body. However, as illustrated in FIG. 21, the first expandable unit 130 and the second expandable unit 140 may also be arranged, for example, in the cardia M7 which is located on the upper part of the stomach M1. Such arrangement makes it possible to reduce the amount of an introduced object such as food that is introduced into a living body and passes through the stomach M1. Therefore, the digestion and absorption of nutrients in the stomach M1 can be suppressed. As a result, it is possible to further improve the therapeutic effect obtained by the digestive tract device 100. Also when balloon type retention means such as the first expandable unit 130 and the second expandable unit 140 is not used as the retention unit 120, the retention of the digestive tract device can be carried out in the cardia M7.

When the first expandable unit 130 and the second expandable unit 140 are retained in the cardia M7, the retention operation is performed in the same manner as in the case in which the first expandable unit 130 and the second expandable unit 140 are retained in the pyloric ring M2. To briefly explain, the second expandable unit 140 is expanded on the distal side of the cardia M7, the digestive tract device 100 is then pulled toward the proximal side of the cardia M7 to hold the second expandable unit 140 on the cardia M7, and the first expandable unit 130 is then expanded on the proximal side of the cardia M7. In such a procedure, as illustrated, the expandable units 130, 140 are fitted respectively into the proximal side and the distal side of the cardia M7. As a result, it is possible to stably retain the digestive tract device 100 for a relatively long period of time.

In this alternative, the digestive tract device 100 according to the first embodiment has been described as an example. However, the alternative can also be applied to the digestive tract devices according to the second and third embodiments and fourth and fifth embodiments (described below) in the same manner.

Fourth Embodiment

Next, a digestive tract device 500 according to a fourth embodiment representing another example of the digestive tract device disclosed here will be described. The digestive tract device 500 according to the fourth embodiment differs from each of the digestive tract devices according to the above embodiments in the arrangement position of a retention unit. A detailed description of the components already described in the first to third embodiments will not be repeated.

Figure 22:
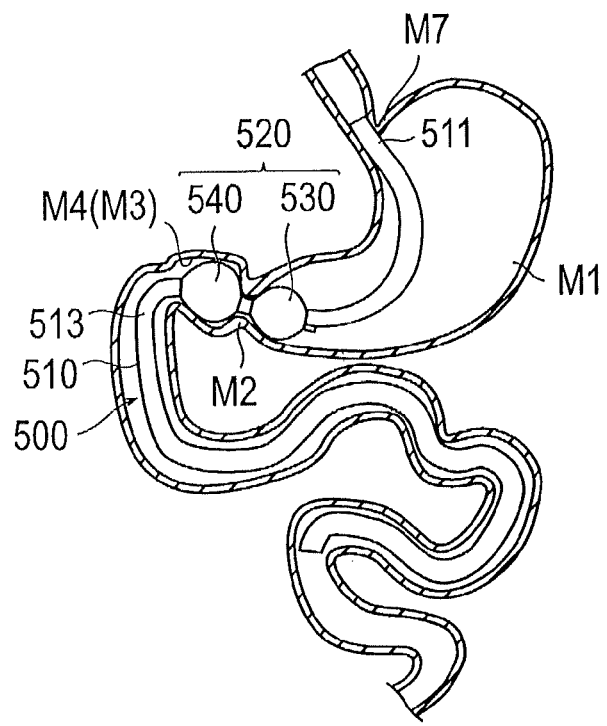
FIG. 22 is a cross-sectional view that illustrates a state in which a digestive tract device according to a fourth embodiment, representing another example of the digestive tract device disclosed here, is retained in the digestive tract.

In the digestive tract devices according to the first to third embodiments, the retention unit which includes the first expandable unit and the second expandable unit are arranged on the base end side in the penetration direction (axial direction) of the tubular portion. However, as illustrated in FIG. 22, a retention unit 520 is arranged in a predetermined region between the base end and the tip of a tubular portion 510 in the digestive tract device 500. The fourth embodiment is the same as the first to third embodiments in that the digestive tract device 500 can be retained inside a living body by arranging expandable units 530, 540 which constitute the retention unit 520 so as to sandwich the pyloric ring M2.

The tubular portion 510 includes a proximal part 511 which is provided on the proximal side with respect to the first expandable unit 530 and a distal part 513 which is provided on the distal side with respect to the second expandable unit 540. As illustrated, when using the digestive tract device 500, the distal part 513 of the tubular portion 510 can be arranged in the duodenum M3. On the other hand, the proximal part 511 of the tubular portion 510 can be arranged so as to extend to the stomach M1, the cardia M7 located on the upper side (proximal side) of the stomach M1, and the upper side with respect to the cardia M7. When the proximal part 511 of the tubular portion 510 is arranged in this manner, an introduced object such as food introduced into a living body flows into the tubular portion 510 at a position located on the proximal side with respect to the stomach M1. Therefore, the amount of the introduced object passing through the stomach M1 decreases. As a result, it is possible to suppress the digestion and absorption of nutrients in the stomach M1 and further improve the therapeutic effect obtained by the digestive tract device 500. The length of the proximal part 511 of the tubular portion 510 is not particularly limited. However, when reducing the digestion and absorption of nutrients in the stomach M1 as described above, the proximal part 511 is preferably formed to have a length that enables the proximal part 511 to extend to the stomach M1 and the cardia M7.

The proximal part 511 of the tubular portion 510 may be integrally connected to the digestive tract device 500 at the stage of introducing the digestive tract device 500 into a living body, or may also be connected to the digestive tract device 500 inside a living body after introducing the digestive tract device 500 into the living body. For example, when the digestive tract device 500 and the proximal part 511 of the tubular portion 510 are integrally formed, it is possible to employ a configuration in which the proximal part 511 of the tubular portion 510 can be folded in a bellows-like form and extend toward the cardia M7 after introducing the proximal part 511 into a living body.

Further, for example, when the digestive tract device 500 and the proximal part 511 of the tubular portion 510 can be connected to and separated from each other, it is possible to employ a configuration in which the connection and separation can be relatively easily performed using screwing-type or fitting type mechanical means. The connection/separation operation can be performed, for example, using an endoscope while confirming an image obtained by the endoscope. That is, the endoscope can be used to provide an image that allows the operator to visually observe the connection/separation operation. The connectable/separable configuration also makes it possible to adjust the efficacy and the effect obtained by the digestive tract device 500 after the digestive tract device 500 is placed inside a living body by connecting or separating the proximal part 511 to or from the digestive tract device 500 depending on the symptom of a patient to whom the digestive tract device 500 is applied.

Further, for example, it is also possible to embed a shape-memory metal wire or the like in the proximal part 511 of the tubular portion 510, or place a ring-shaped anchor member on an opening end of the proximal part 511, the opening end facing the cardia M7. Such a configuration makes it possible to stably maintain the proximal part 511 of the tubular portion 510 in a standing state (extending state) toward the cardia M7.

Fifth Embodiment

Next, a digestive tract device 600 according to a fifth embodiment, representing another example of the digestive tract device disclosed here, will be described. The digestive tract device 600 according to the fifth embodiment differs from each of the digestive tract devices according to the above embodiments in the configurations of a length adjustment unit and a retention unit. A detailed description of the components already described in the first to fourth embodiments will not be repeated.

Figure 23:
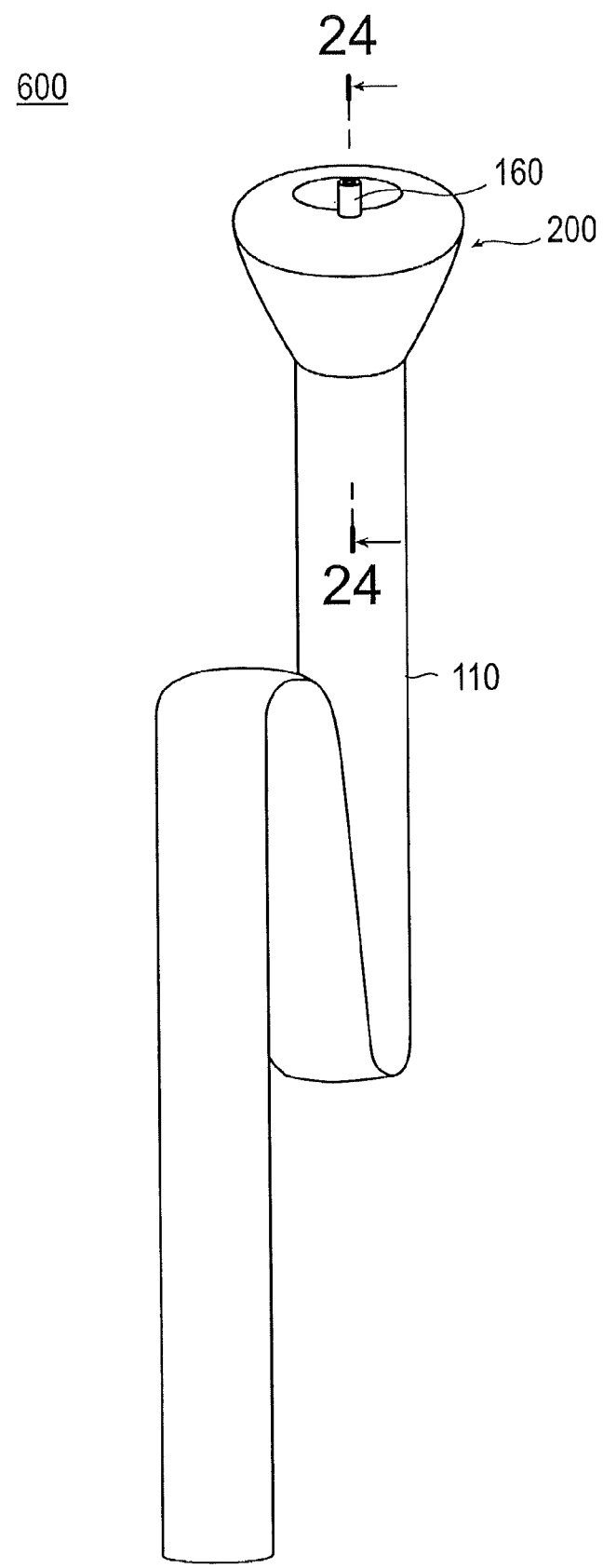
FIG. 23 is a perspective view that illustrates a digestive tract device according to a fifth embodiment representing an additional example of the digestive tract device disclosed here.
Figure 24:
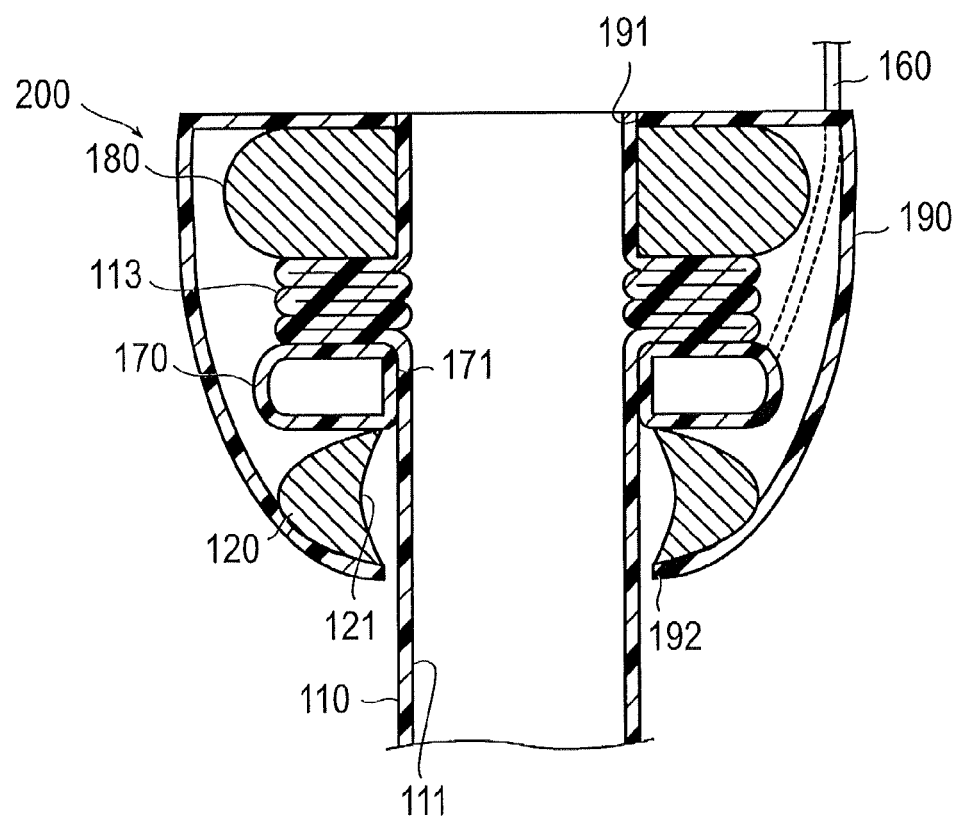
FIG. 24 is a cross-sectional view taken along the section line 24-24 of FIG. 23 and illustrates a state before a folded portion of a tubular portion is unfolded.

As illustrated in FIGS. 23 and 24, the digestive tract device 600 according to the present embodiment is provided with a flexible tubular portion 110 which is formed in a tubular shape and has an axially extending through hole 111, a retention unit 120 which is provided on one end in the penetration direction (axial direction) of the tubular portion 110, and a length adjustment unit 200 which adjusts the length of the tubular portion 110.

As illustrated in FIGS. 23 and 24, a folded portion 113 which is folded in the longitudinal direction and the through hole 111 are formed on the tubular portion 110. Further, an insertion hole 121 through which the tubular portion 110 is inserted is formed on the retention unit 120 which holds the tubular portion 110 inside a living body.

The digestive tract device 600 further includes a deformable unit 170 which is arranged on the base end side of the tubular portion 110 with respect to the retention unit 120. The deformable unit 170 is deformable from a first state as an expanded state (refer to FIG. 24) to a second state as a contracted state (refer to FIG. 25). The digestive tract device 600 further includes a stopper 180 which is arranged on the base end side of the tubular portion 110 with respect to the deformable unit 170, sandwiches the folded portion 113 of the tubular portion 110 with the deformable unit 170, and is locked to or in contact with the retention unit 120 when the deformable unit 170 is deformed from the expanded state to the contracted state. Further, in the digestive tract device 600, it is possible to unfold the folded portion 113 of the tubular portion 110 toward the tip side of the tubular portion 110 while holding the tubular portion 110 inside a living body by deforming the deformable unit 170 from the expanded state to the contracted state with the tubular portion 110 held inside a living body by the retention unit 120.

The folded portion 113 of the tubular portion 110 is formed by folding back the tubular portion 110 a plurality of times in the longitudinal direction of the tubular portion 110 (the penetration direction of the through hole, the up-down direction in FIGS. 23 and 24). The number of times of folding the tubular portion 110 and the length of the folded portion 113 are not particularly limited, and can be set to any number and length depending on the entire length of the tubular portion 110 that is required after being placed in the living body.

The retention unit 120 includes a ring-shaped member that can be locked to the duodenum M3 or the like inside a living body. The retention unit is an enlarged member that is enlarged relative to an axially adjacent portion of the tubular body so that the enlarged member can engage a portion of the digestive tract to fix the location of the tubular body in the digestive tract. A part of the tubular portion 110 is inserted through the insertion hole 121 formed on the retention unit 120. The retention unit 120 is formed of a hard resin material.

However, the material of the retention unit 120 is not particularly limited as long as it can hold the tubular portion 110 to a living body.

In the digestive tract device 600, the deformable unit 170 which is locked to (in contact with) the retention unit 120 is composed of a balloon which is expanded by injecting fluid into the balloon and contracted by discharging the injected fluid from the balloon. Further, for example, a ring-shaped balloon which has a center hole 171 through which the tubular portion 110 can be inserted is used as the balloon. The fluid used for deforming the deformable unit 170 is, for example, a physiological saline solution. However, the fluid may also be another liquid, gas such as air, liquid or gas in which a solid is dispersed, and an aggregate of particles. Further, the fluid may be a mixture of liquid and gas so as to absorb a strong compression force from the digestive tract by the compressive gas while maintaining a strong holding power or holding strength by the non-compressive liquid.

The balloon as the deformable unit 170 can be configured, for example, to have a larger outer diameter than the insertion hole 121 of the retention unit 120 in an expanded state and a smaller outer diameter than the insertion hole 121 of the retention unit 120 in a contracted state. The outer diameter of the deformable unit 170 in an expanded state and a contracted state is not particularly limited. For example, when the diameter of the insertion hole 121 is approximately 20 mm, the outer diameter of the deformable unit 170 can be approximately 25 mm in an expanded state and approximately 18 mm in a contracted state.

A conventionally known balloon which is formed of, for example, polyamide, polyethylene terephthalate, high-density polyethylene, nylon elastomer, or polyether elastomer can be used as the balloon.

An inlet unit 160 for feeding the fluid into the inside of the balloon is liquid-tightly/air-tightly connected to the balloon as the deformable unit 170. For example, a known resin tube thorough which the fluid can flow is used as the inlet unit 160. Further, a check valve or the like which prevents the backflow of the fluid can be provided in the inlet unit 160.

The stopper 180 includes a ring-shaped member which is arranged on the base end side with respect to the deformable unit 170. The stopper 180 is arranged so that the folded portion 113 of the tubular portion 110 is sandwiched between the stopper 180 and the deformable unit 170. Further, the stopper 180 can be attached to the upper end of the folded portion 113 of the tubular portion 110 by a known method such as bonding and fusion. Although the material of the stopper is not particularly limited, the stopper can be formed of, for example, a hard resin material.

When introducing the digestive tract device 600 into a living body, the folded portion 113 of the tubular portion 110, the retention unit 120, the deformable unit 170, and the stopper 180 are covered by a cover member 190. Accordingly, it is possible to prevent the components from being caught on a living body when introducing the components into the living body, and smoothly introduce the digestive tract device 600 into the living body. In the description of the specification, the cover member 190 and the components housed inside the cover member 190 are collectively referred to as the length adjustment unit 200 for descriptive purpose.

The inlet unit 160 which is connected to the deformable unit 170 is lead out to the base end side from the cover member 190. A lower end part 192 of the cover member 190 is fixed to the retention unit 120 by a known method such as bonding and fusion. An upper end part 191 of the cover member 190 is fixed to the stopper 180 by a known method such as bonding and fusion. Although the material of the cover member 190 is not particularly limited, for example, the cover member 190 can be formed of the same material as the constituent material of the tubular portion 110.

Next, an operation of the length adjustment unit 200 when unfolding the folded portion 113 of the tubular portion 110 will be described.

As illustrated in FIG. 24, the folded portion 113 formed on the tubular portion 110 is sandwiched between the deformable unit 170 in an expanded state and the stopper 180. The retention unit 120 can be locked to a predetermined position inside a living body in a state in which the folded portion 113 is formed on the tubular portion 110.

Figure 25:
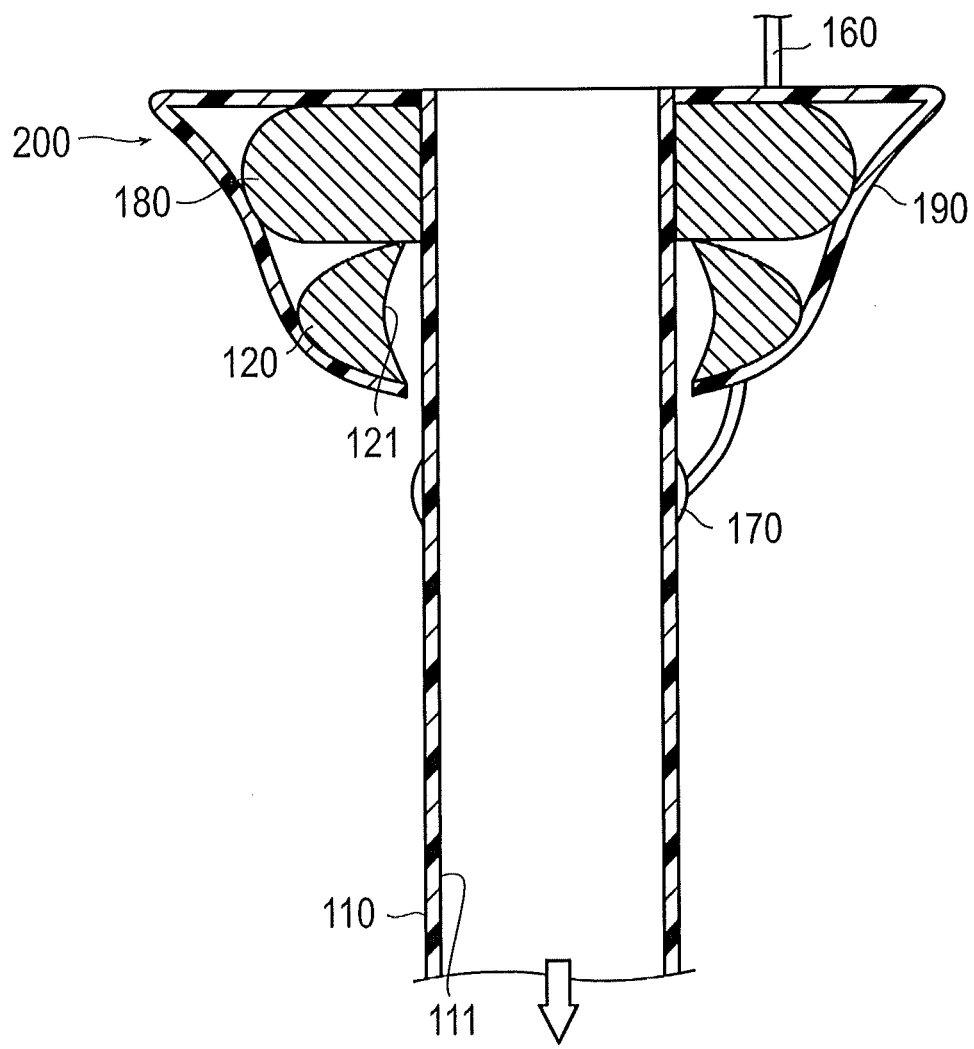
FIG. 25 is a cross-sectional view taken along the section line 24-24 of FIG. 23 and illustrates a state in which the folded portion of the tubular portion is unfolded.

As illustrated in FIG. 25, the deformable unit 170 is contracted to unfold the folded portion 113 of the tubular portion 110 toward the tip side. At this point, the deformable unit 170 passes through the insertion hole 121 of the retention unit 120. The stopper 180 slides toward the tip side and is locked to the retention unit 120. The retention unit 120 maintains the locked state to the living body regardless of the unfolding of the folded portion 113 of the tubular portion 110. Accordingly, it is possible to extend the tubular portion 110 while maintaining the tubular portion 110 in a held state to the living body by the retention unit 120.

Next, a method for placing the digestive tract device 600 according to the present embodiment inside the digestive tract will be described.

Figure 26:
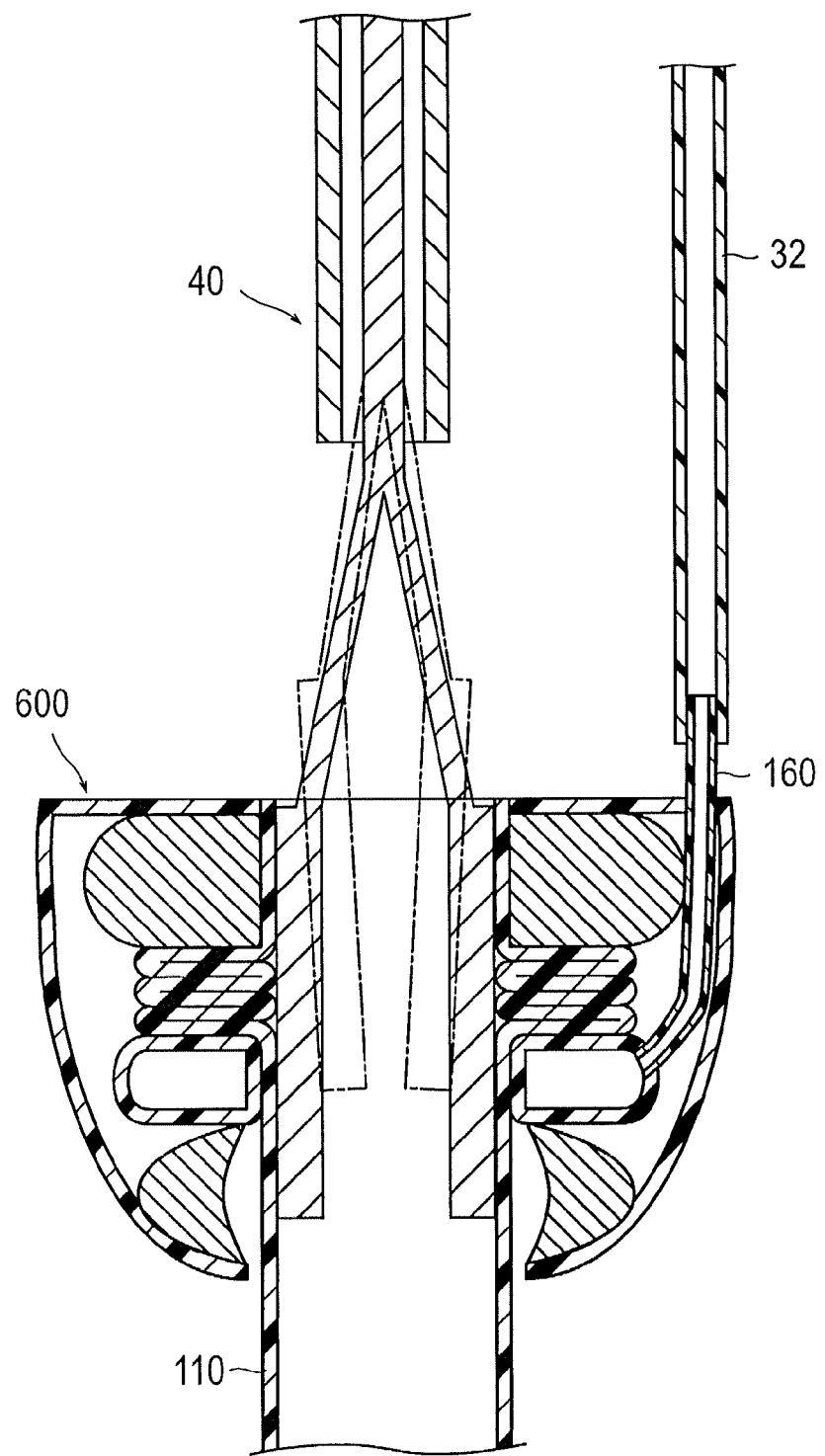
FIG. 26 is a cross-sectional view that illustrates a state in which a grasping member and a supply tube are connected to the digestive tract device according to the fifth embodiment.

As illustrated in FIG. 26, the placement of the digestive tract device 600 can be performed using the digestive tract device placing system described above (refer to FIG. 4).

Before inserting the digestive tract device 600 into the living body, the setting of the length adjustment unit 200 is performed. First, the folded portion 113 to be unfolded after the placement is previously formed on the tubular portion 110. Then, the balloon as the deformable unit 170 is maintained in an expanded state by the fluid supply device 30 which is provided in the digestive tract device placing system to hold the folded portion 113 in a folded state. The folding amount of the tubular portion 110 (the number of times of folding the tubular portion and the length of the folded portion) and the like may be set at the stage of preparing the introduction or may also be previously set at the time of manufacturing the digestive tract device 600. Further, the supply tube 32 provided in the digestive tract device placing system may be detached from the inlet unit 160 after expanding the deformable unit 170.

Next, the tip side of the tubular portion 110 of the digestive tract device 600 is folded. The folded region is not a region constituting the folded portion 113 used in the length adjustment after the placement, but a region that is formed prior to the introduction for improving the introduction property into a living body. Further, as will be described below, the folded state is released at the time of the introduction so as to be unfolded toward the distal side of the duodenum.

Figure 27:
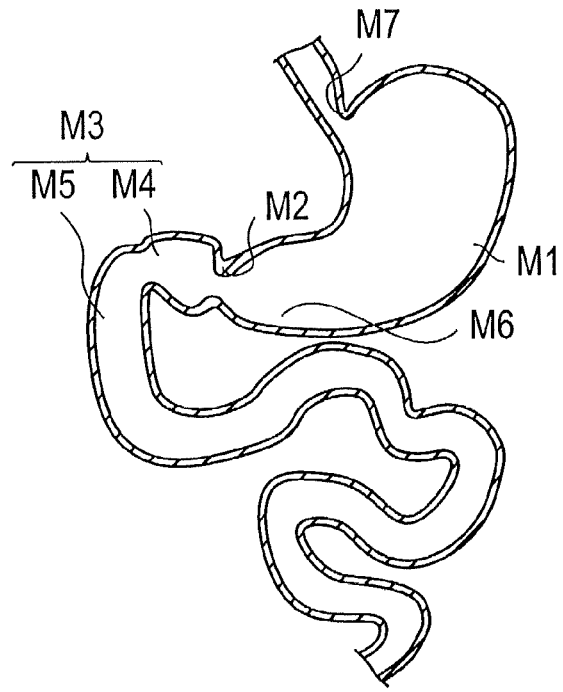
FIG. 27 is a schematic cross-sectional view that illustrates a part of the digestive tract.
Figure 28:
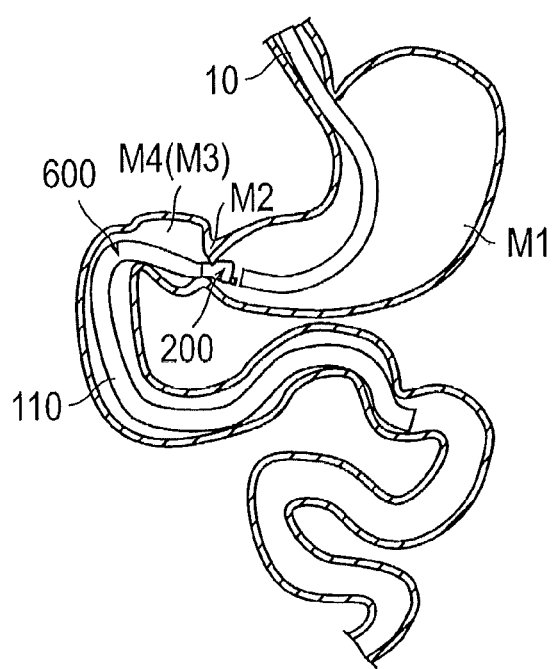
FIG. 28 is a schematic cross-sectional view that illustrates a state in which the digestive tract device is inserted into the digestive tract through an endoscope.

Then, the endoscope 10 is inserted through the mouth or nose, and moved forward until the tip of the endoscope 10 is located near the pyloric ring M2 while confirming an image as illustrated in FIGS. 27 and 28, that is while confirming a distal position of the endoscope 10. After the distal position of the endoscope 10 is determined or identified, the digestive tract device 100 is introduced the digestive tract through the channel of the endoscope 10. The digestive tract device 600 is grasped by the grasping device 40, and inserted into the channel 12 of the endoscope 10. Further, the grasping device 40 is pushed to move the digestive tract device 600 to the tip side. The digestive tract device 600 may be previously inserted into the channel 12 using the grasping device 40 before inserting the endoscope 10 through the mouth or nose.

Then, the digestive tract device 600 is allowed to project distally beyond the tip of the endoscope 10 toward the duodenal bulb M4. At this point, the retention unit 120 provided in the length adjustment unit 200 is held on the pyloric ring M2 and locked thereto. Accordingly, the tubular portion 110 can be held in a living body.

When the digestive tract device 600 is placed near the pyloric ring M2, the tip side of the tubular portion 110 extends to the distal side by the peristaltic movement of the duodenum M3.

Figure 29:
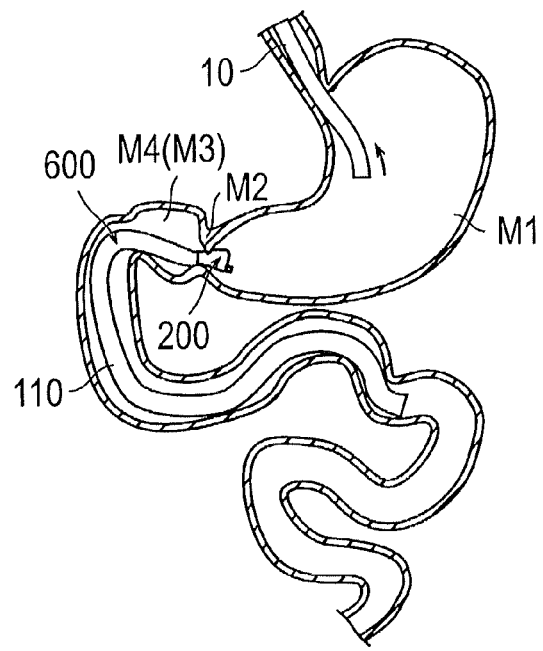
FIG. 29 is a schematic cross-sectional view that illustrates a state in which the endoscope is removed from the inside of the digestive tract.

Thereafter, the operation unit 42 of the grasping device 40 is operated to release the grasping of the digestive tract device 600. Then, as illustrated in FIG. 29, the endoscope 10 and the grasping device 40 are pulled out of the digestive tract and the retention procedure is completed.

Figure 30:
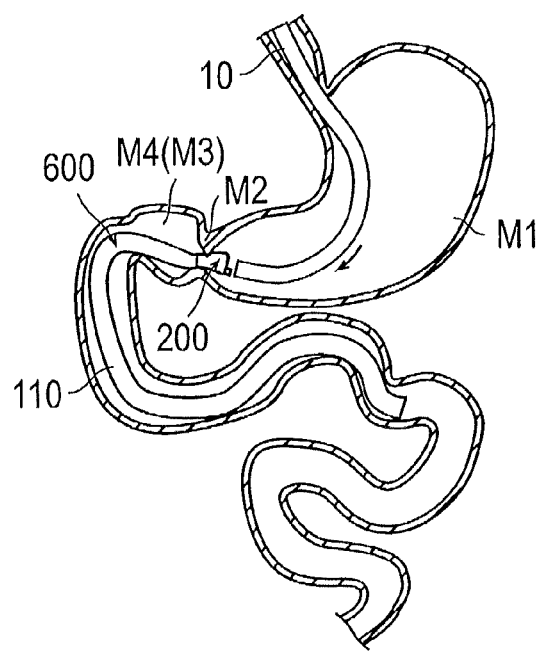
FIG. 30 is a schematic cross-sectional view that illustrates an operation of bringing the supply tube together with the endoscope close to the digestive tract device retained in the digestive tract.

When adjusting the length of the tubular portion 110 of the digestive tract device 600 after the placement, as illustrated in FIG. 30, the endoscope 10 is again introduced up to the vicinity of the pyloric ring M2.

Figure 31:
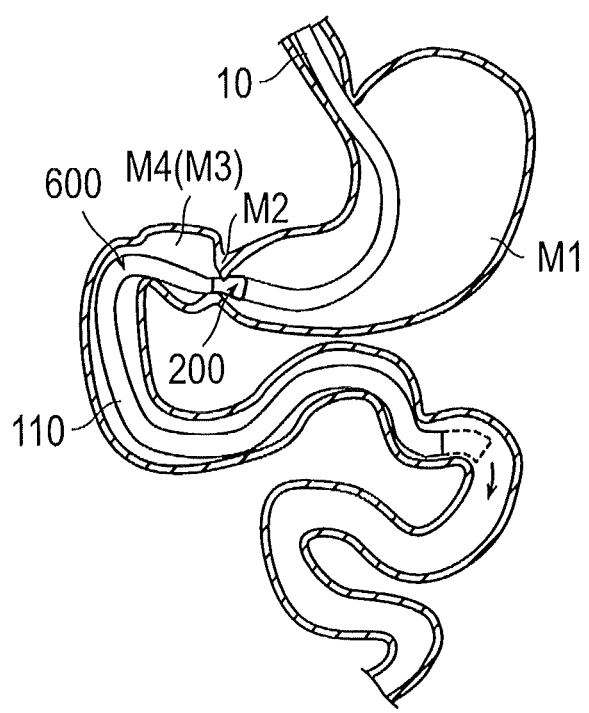
FIG. 31 is a schematic cross-sectional view that illustrates a state in which a folded portion of the tubular portion is unfolded with the digestive tract device retained in the digestive tract.

Then, as illustrated in FIG. 31, the supply tube 32 is connected to the inlet unit 160 of the digestive tract device 600 while confirming an image obtained by the endoscope 10 (refer to FIG. 26) identifying the position of the endoscope. Then, the fluid filled inside the deformable unit 170 is discharged from the deformable unit 170 to the outside to contract the deformable unit 170. Accordingly, unfolding the folded portion 113 of the tubular portion 110 toward the tip side makes it possible to increase the retained length of the tubular portion 110 inside the duodenum M3.

As described above, the digestive tract device 600 according to the present embodiment can unfold the folded portion 113 of the tubular portion 110 toward the tip side of the tubular portion 110 while holding the tubular portion 110 inside a living body by deforming the deformable unit 170 which is locked to the retention unit 120 with the tubular portion 110 in which the folded portion 113 is formed held inside a living body by the retention unit 120. When reducing the digestion and absorption in the small intestine after the tubular portion 110 is placed, it is not necessary to perform a complicated operation of replacing the tubular portion 110. Therefore, it is possible to rather easily adjust the length of the tubular portion 110 after the placement and reduce the burden on a living body associated with the length adjustment.

Further, when the deformable unit 170 is composed of a balloon that is deformable from an expanded state in which the balloon is locked to the retention unit 120 and a contracted state in which the locked state to the retention unit 120 is released, the folded portion 113 of the tubular portion 110 can be unfolded toward the tip side by a rather simple operation of merely operating the expansion and contraction of the balloon.

Also, when the balloon as the deformable unit 170 is a ring-shaped balloon through which the tubular portion 110 is inserted, a balloon which can be relatively easily manufactured and has a general structure can be used as the deformable unit 170. Therefore, it is possible to reduce the manufacturing cost and simplify the manufacturing operation in the digestive tract device 600.

Further, the folded portion 113 of the tubular portion 110, the retention unit 120, the deformable unit 170, and the stopper 180 are covered by the cover member 190 when introducing the digestive tract device 600 into a living body, it is possible to prevent the components from being caught on the living body, and therefore smoothly perform an operation of introducing the digestive tract device 600.

The digestive tract device 600 according to the fifth embodiment can be appropriately modified.

The digestive tract device 600 according to the fifth embodiment is the same as the digestive tract devices according to the first to fourth embodiments in that the arrangement position of the retention unit 120 is not limited to the pyloric ring M2 and the retention unit 120 can be arranged in the duodenal bulb M4 and the cardia M7 (refer to FIGS. 21 and 22), and the retention unit and the length adjustment unit can be provided not only in the base end side in the penetration direction of the tubular portion 110, but also in a predetermined region between the base end and the tip of the tubular portion 110.

Further, the holding power for holding the tubular portion 110 inside a living body can also be improved by using a balloon or a stent for holding the tubular portion 110 inside a living body together with the retention unit 120.

Although there has been described the configuration in which the deformable unit 170 is composed of a balloon, the deformable unit 170 is not limited to only a balloon as long as it has a configuration capable of unfolding the folded portion 113 of the tubular portion 110 toward the tip side along with the deformation from the first state to the second state. For example, the deformable unit may be formed of a material that is contracted or discomposed by liquid, light, ultrasonic waves or the like. Allowing liquid, light, or ultrasonic waves to act on the deformable unit after the placement to cause the deformation of the deformable unit makes it possible to extend the tubular portion 110.

When the deformable unit is formed of a material that is deformed by liquid, the application of the liquid can be performed through the inlet unit 160. As the constituent material of the deformable unit when using liquid, there can be used pH-degradable polymers including poly (methacrylic acid-methyl methacrylate), a poly (methyl acrylate-methyl methacrylate-methacrylate acid) copolymer and a methacrylate acid-methacrylate acid methyl copolymer, a water-disintegrable polymer including polyvinyl alcohol, and biodegradable polymers including polylactic acid and polyvinyl alcohol. Further, light or ultrasonic waves may be applied by inserting an irradiation fiber into the inlet unit 160, or may also be applied from the inside of the tubular portion 110 so as to be transmitted through the tubular portion 110 without using the inlet unit 160. Examples of the constituent material of the deformable unit when using light include polyketone, a benzyl group containing polymer, and azobenzene. Examples of the constituent material of the deformable unit when using ultrasonic waves include polystyrene, polymethylmethacrylate, and pullulan.

Further, it is also possible to employ a configuration in which the deformable unit is deformed not by an artificial operation, but automatically with the lapse of time after introducing the digestive tract device into a living body. For example, when the deformable unit is formed of a material that is expanded by injecting fluid such as air and liquid into the deformable unit and gradually transmitted after the injection of the fluid, the deformable unit can be deformed without performing an artificial operation. Since the deformable unit is gradually contracted with the lapse of time, the tubular portion can be extended in stages along with the contraction.

In the fifth embodiment, there has been described the configuration in which the contracted deformable unit 170 passes through the insertion hole 121 of the retention unit 120 and moves to the tip side with respect to the retention unit 120. However, for example, a configuration in which the deformable unit 170 is locked to the retention unit 120 without passing through the insertion hole 121 of the retention unit 120 may also be employed.

There has also been described the configuration in which the single folded portion 113 is formed on the tubular portion 110. However, for example, there may also be employed a configuration in which a plurality of folded portions 113 are formed in the longitudinal direction and a plurality of deformable units 170 are provided to adjust the length of the tubular portion 110 in a multistage manner.

Further, although there has been described the configuration in which the stopper 180 is locked to the retention unit 120 when unfolding the folded portion 113 of the tubular portion 110, for example, it is also possible to employ a configuration in which the cover member 190 is locked to the retention unit 120 without placing the stopper 180. Such a configuration makes it possible to allow the cover member 190 to function as a stopper, and downsize the length adjustment unit 200.

Hereinbelow, additional comments on the digestive tract device according to the fifth embodiment will be described.

A digestive tract device is disclosed which includes: a tubular portion having a through hole and a folded portion folded in the longitudinal direction; a retention unit that has an insertion hole through which the tubular portion is inserted and holds the tubular portion inside a living body; a deformable unit that is arranged on the base end side of the tubular portion with respect to the retention unit and deformable from a first state to a second state; and a stopper that is arranged on the base end side of the tubular portion with respect to the deformable unit, sandwiches the folded portion of the tubular portion with the deformable unit, and is locked to the retention unit when the deformable unit is deformed from the first state to the second state, wherein the folded portion of the tubular portion can be unfolded toward the tip side of the tubular portion while holding the tubular portion inside a living body by deforming the deformable unit from the first state to the second state with the tubular portion held inside the living body by the retention unit.

The deformable unit includes a balloon that is deformable from an expanded sate as the first state to a contracted state as the second state.

The balloon includes a ring-shaped balloon through which the tubular portion can be inserted, and a cover member covers the folded portion of the tubular portion, the retention unit, the deformable unit, and the stopper when introducing the digestive tract device into a living body.

The detailed description above describes embodiments and modifications of a digestive tract device representing examples of the digestive tract device of the present invention. The invention is not limited, however, to the precise embodiments and variations described. Various changes, modifications and equivalents can effected by one skilled in the art without departing from the spirit and scope of the invention as defined in the accompanying claims. It is expressly intended that all such changes, modifications and equivalents which fall within the scope of the claims are embraced by the claims.

What is claimed is:

1. A digestive tract device comprising:
a tubular portion possessing a through hole;
a retention unit fixed on a distal portion of the tubular portion and holding the tubular portion inside a living body;
a length adjustment unit adjusting the length of the tubular portion;
the length adjustment unit including a holding unit holding at least a part of the tubular portion to adjust the length of the tubular portion;
the tubular portion including a main body having a tip communicating with the through hole and a folded-back portion in which the main body is folded back on itself in the longitudinal direction; and
the holding unit holding the folded-back portion in a folded-back state with the tip opening open.

2. The digestive tract device according to claim 1, wherein:
the holding unit includes at least a first holding region and a second holding region having different holding strengths for holding the folded-back portion in a folded-back state; and
the first holding region on the base end side of the tubular portion with respect to the second holding region and the holding strength of the first holding region is greater than the holding strength of the second holding region.

3. The digestive tract device according to claim 1, wherein the holding unit includes a thermally-fused portion to which the folded-back portion is bonded by thermal fusion.

4. The digestive tract device according to claim 1, wherein a tip end of the main body continuous with the folded-back portion is located on a tip side of the tubular portion with respect to a tip-side folding back position of the folded-back portion when the holding unit holds the folded-back portion.

5. The digestive tract device according to claim 4, wherein an axial length between the tip-side folding back position of the folded-back portion and the tip end of the main body is longer than an axial length between the tip-side folding back position of the folded-back portion and the retention unit.

6. The digestive tract device according to claim 1, wherein a tip end of the main body continuous with the folded-back portion is located on a base end side of the tubular portion with respect to a tip-side folding back position of the folded-back portion when the holding unit holds the folded-back portion.

7. The digestive tract device according to claim 1, wherein the holding unit is configured to hold at least a part of the tubular portion in a lifted state toward a base end side of the tubular portion.

8. The digestive tract device according to claim 7, wherein the holding unit includes at least one first locking piece attached to the tubular portion and a second locking piece attached to the tubular portion at a position on a tip side with respect to the at least one first locking piece and freely engageable with and disengageable from the at least one first locking piece.

9. The digestive tract device according to claim 8, wherein the second locking piece is freely deformable between a first shape that enables the second locking piece to move to the base end side of the tubular portion beyond the at least one first locking piece and a second shape that enables at least a part of the second locking piece to be locked to the at least one first locking piece on the base end side with respect to the at least one first locking piece.

10. The digestive tract device according to claim 9, wherein:
the at least one first locking piece and the second locking piece each have insertion holes through which an introduced object introduced into the tubular portion from outside of a living body can pass, the first locking piece and the second locking piece being arranged inside the tubular portion; and
the second locking piece is freely deformable between the first shape that enables the second locking piece to be inserted through the insertion hole of the at least one first locking piece and the second shape that enables the second locking piece to be locked to the at least one first locking piece.

11. The digestive tract device according to claim 8, wherein the at least one first locking piece comprises a plurality of first locking pieces arranged in spaced apart relation to one another in the longitudinal direction of the tubular portion.

12. The digestive tract device according to claim 9, wherein the second locking piece comprises an elastic member that is deformable between the first shape and the second shape.

13. The digestive tract device according to claim 1, wherein the retention unit is provided on a base end side in a penetration direction of the tubular portion.

14. The digestive tract device according to claim 1, wherein the retention unit is provided in a predetermined region between a base end and a tip of the tubular portion.

15. A digestive tract device positionable in a digestive track of a living body comprising:
   a tubular portion configured to be positioned in the digestive tract of the living body, the tubular portion possessing a distal tip and a through hole opening at the distal tip of the tubular body;
   a retention unit positioned on a distal portion of the tubular portion, the retention unit comprising one of: i) an outwardly expandable member that is outwardly expandable to an expanded state larger than a portion of the digestive tract when the distal portion of the tubular body is located in the digestive tract to hold the tubular body in the digestive tract; and ii) an expanded member larger than the portion of the digestive tract when the distal portion of the tubular body is located in the digestive tract to hold the tubular body in the digestive tract;
   the tubular body including a folded portion at which the tubular body is folded in a folded condition of the tubular body, and the folded portion of the tubular body being held in the folded condition; and
   the folded condition of the tubular body being releasable when the tubular body in the folded condition is positioned in the digestive tract to increase a length of the tubular body.

16. The digestive tract device according to claim 15, wherein the folded portion of the tubular body includes at least a first holding region and a second holding region having different holding strengths at which the folded portion is held in the folded condition.

17. The digestive tract device according to claim 15, wherein the retention unit is a pair of spaced apart outwardly expandable balloons.

18. A method comprising:
   introducing a tip end portion of a tubular body into a digestive tract in a living body, the tubular portion possessing a through hole, the tubular body including a folded portion at which the tubular body is folded;
   the tubular body with the folded portion being moved in the digestive tract to a predetermined position in the digestive tract; and
   increasing a length of the tubular body located at the predetermined position in the digestive tract by unfolding the folded portion.

19. The method according to claim 18, further comprising retaining the tubular body is retained at the predetermined position in the digestive tract before increasing the length of the tubular body.

* * * * *